US012653945B2

(12) United States Patent
Kamrava et al.

(10) Patent No.: US 12,653,945 B2
(45) Date of Patent: Jun. 16, 2026

(54) DRIVE MECHANISM FOR POSITIVE DISPLACEMENT PUMPS

(71) Applicant: INSULET CORPORATION, Acton, MA (US)

(72) Inventors: Soroush Kamrava, Everett, MA (US); Steven Cardinali, Tewksbury, MA (US); Jeffrey Barnes, Medford, MA (US)

(73) Assignee: INSULET CORPORATION, Acton, MA (US)

( * ) Notice: Subject to any disclaimer, the term of this patent is extended or adjusted under 35 U.S.C. 154(b) by 780 days.

(21) Appl. No.: 18/047,068

(22) Filed: Oct. 17, 2022

(65) Prior Publication Data

US 2023/0117504 A1    Apr. 20, 2023

Related U.S. Application Data

(60) Provisional application No. 63/256,714, filed on Oct. 18, 2021.

(51) Int. Cl.
*A61M 5/142* (2006.01)
*A61M 5/158* (2006.01)
(Continued)

(52) U.S. Cl.
CPC .... *A61M 5/14216* (2013.01); *A61M 5/14244* (2013.01); *A61M 5/158* (2013.01);
(Continued)

(58) Field of Classification Search
CPC . A61M 2205/0266; A61M 2005/31518; F04B 9/04; F16H 21/50
See application file for complete search history.

(56) References Cited

U.S. PATENT DOCUMENTS 1,441,508 A    1/1923    Jensen
2,198,666 A    4/1940    Gruskin
(Continued)

FOREIGN PATENT DOCUMENTS

CA          606281 A    10/1960
CN          1375338 A    10/2002
(Continued)

OTHER PUBLICATIONS

International Search Report and Written Opinion for PCT/US2018/014351, mailed on Jun. 4, 2018, 9 pages.
(Continued)

*Primary Examiner* — Deanna K Hall
(74) *Attorney, Agent, or Firm* — GOODWIN PROCTER LLP

(57) ABSTRACT

A novel embodiment of a drive mechanism for use in a pump, for example, of the type that would be used in a wearable drug delivery system, comprises, a cylindrically-shaped slider element configured with a channel on a circumferential surface thereof defining one or more zig-zag-shaped tracks therethrough. One or more pegs are engaged within the tracks, such that a back and forth longitudinal motion of the slider element along a radial axis of the cylinder causes movement of the pegs along one of the tracks through the channel, thus providing a movement of the pegs around the circumference of the cylinder which imparts a rotational motion to a header element disposed co-axially with the slider. The header element is in turn connected to a gear train, for example, a planetary gear box, which is coupled to the pump via a linkage or other type of mechanism.

18 Claims, 15 Drawing Sheets

(51) Int. Cl.
 F04B 9/04    (2006.01)
 F16H 21/50   (2006.01)
(52) U.S. Cl.
 CPC ............... F04B 9/04 (2013.01); F16H 21/50
  (2013.01); *A61M 2202/0486* (2013.01); *A61M*
            *2205/502* (2013.01)

(56)       References Cited

U.S. PATENT DOCUMENTS

| | | | |
|---|---|---|---|
| 2,752,918 | A | 7/1956 | Uytenbogaar |
| 3,176,712 | A | 4/1965 | Ramsden |
| 3,297,260 | A | 1/1967 | Barlow |
| 3,464,359 | A | 9/1969 | King |
| 3,885,662 | A | 5/1975 | Schaefer |
| 3,946,732 | A | 3/1976 | Hurscham |
| 3,947,692 | A | 3/1976 | Payne |
| 3,993,061 | A | 11/1976 | OLeary |
| 4,108,177 | A | 8/1978 | Pistor |
| 4,152,098 | A | 5/1979 | Moody et al. |
| 4,210,173 | A | 7/1980 | Choksi et al. |
| 4,221,219 | A | 9/1980 | Tucker |
| 4,257,324 | A | 3/1981 | Stefansson et al. |
| 4,268,150 | A | 5/1981 | Chen |
| 4,277,226 | A | 7/1981 | Archibald |
| 4,313,439 | A | 2/1982 | Babb et al. |
| 4,371,790 | A | 2/1983 | Manning et al. |
| 4,417,889 | A | 11/1983 | Choi |
| 4,424,720 | A | 1/1984 | Bucchianeri |
| 4,435,173 | A | 3/1984 | Siposs et al. |
| 4,475,905 | A | 10/1984 | Himmelstrup |
| 4,498,843 | A | 2/1985 | Schneider et al. |
| 4,507,115 | A | 3/1985 | Kambara et al. |
| 4,551,134 | A | 11/1985 | Slavik et al. |
| 4,562,751 | A | 1/1986 | Nason et al. |
| 4,567,549 | A | 1/1986 | Lemme |
| 4,585,439 | A | 4/1986 | Michel |
| 4,601,707 | A | 7/1986 | Albisser et al. |
| 4,634,427 | A | 1/1987 | Hannula et al. |
| 4,671,429 | A | 6/1987 | Spaanderman et al. |
| 4,678,408 | A | 7/1987 | Nason et al. |
| 4,684,368 | A | 8/1987 | Kenyon |
| 4,685,903 | A | 8/1987 | Cable et al. |
| 4,755,169 | A | 7/1988 | Sarnoff et al. |
| 4,766,889 | A | 8/1988 | Trick et al. |
| 4,808,161 | A | 2/1989 | Kamen |
| 4,846,797 | A | 7/1989 | Howson et al. |
| 4,858,619 | A | 8/1989 | Toth |
| 4,898,579 | A | 2/1990 | Groshong et al. |
| 4,908,017 | A | 3/1990 | Howson et al. |
| 4,944,659 | A | 7/1990 | Labbe et al. |
| 4,969,874 | A | 11/1990 | Michel et al. |
| 4,991,743 | A | 2/1991 | Walker |
| 5,007,458 | A | 4/1991 | Marcus et al. |
| 5,020,325 | A | 6/1991 | Henault |
| 5,062,841 | A | 11/1991 | Siegel |
| 5,147,311 | A | 9/1992 | Pickhard |
| 5,178,609 | A | 1/1993 | Ishikawa |
| 5,205,819 | A | 4/1993 | Ross et al. |
| 5,213,483 | A | 5/1993 | Flaherty et al. |
| 5,222,362 | A | 6/1993 | Maus et al. |
| 5,236,416 | A | 8/1993 | McDaniel et al. |
| 5,261,882 | A | 11/1993 | Sealfon |
| 5,261,884 | A | 11/1993 | Stern et al. |
| 5,277,338 | A | 1/1994 | Divall et al. |
| 5,281,202 | A | 1/1994 | Weber et al. |
| 5,346,476 | A | 9/1994 | Elson |
| 5,364,342 | A | 11/1994 | Beuchat et al. |
| 5,388,615 | A | 2/1995 | Edlund et al. |
| 5,433,710 | A | 7/1995 | VanAntwerp et al. |
| 5,503,628 | A | 4/1996 | Fetters et al. |
| 5,520,661 | A | 5/1996 | Lal et al. |
| 5,533,389 | A | 7/1996 | Kamen et al. |
| 5,582,593 | A | 12/1996 | Hultman |
| 5,618,269 | A | 4/1997 | Jacobsen et al. |
| 5,628,309 | A | 5/1997 | Brown |
| 5,637,095 | A | 6/1997 | Nason et al. |
| 5,665,070 | A | 9/1997 | McPhee |
| 5,713,875 | A | 2/1998 | Tanner, II |
| 5,747,350 | A | 5/1998 | Sattler |
| 5,748,827 | A | 5/1998 | Holl et al. |
| 5,776,103 | A | 7/1998 | Kriesel et al. |
| 5,779,676 | A | 7/1998 | Kriesel et al. |
| 5,785,688 | A | 7/1998 | Joshi et al. |
| 5,797,881 | A | 8/1998 | Gadot |
| 5,800,397 | A | 9/1998 | Wilson et al. |
| 5,807,075 | A | 9/1998 | Jacobsen et al. |
| 5,839,467 | A | 11/1998 | Saaski et al. |
| 5,891,097 | A | 4/1999 | Saito et al. |
| 5,897,530 | A | 4/1999 | Jackson |
| 5,906,597 | A | 5/1999 | McPhee |
| 5,911,716 | A | 6/1999 | Rake et al. |
| 5,919,167 | A | 7/1999 | Mulhauser et al. |
| 5,957,890 | A | 9/1999 | Mann et al. |
| 5,961,492 | A | 10/1999 | Kriesel et al. |
| 5,971,963 | A | 10/1999 | Choi |
| 6,019,747 | A | 2/2000 | McPhee |
| 6,050,457 | A | 4/2000 | Arnold et al. |
| 6,068,615 | A | 5/2000 | Brown et al. |
| 6,159,188 | A | 12/2000 | Laibovitz et al. |
| 6,174,300 | B1 | 1/2001 | Kriesel et al. |
| 6,190,359 | B1 | 2/2001 | Heruth |
| 6,200,293 | B1 | 3/2001 | Kriesel et al. |
| 6,352,522 | B1 | 3/2002 | Kim et al. |
| 6,363,609 | B1 | 4/2002 | Pickren |
| 6,375,638 | B2 | 4/2002 | Nason et al. |
| 6,474,219 | B2 | 11/2002 | Klitmose et al. |
| 6,485,461 | B1 | 11/2002 | Mason et al. |
| 6,485,462 | B1 | 11/2002 | Kriesel |
| 6,488,652 | B1 | 12/2002 | Weijand et al. |
| 6,520,936 | B1 | 2/2003 | Mann |
| 6,527,744 | B1 | 3/2003 | Kriesel et al. |
| 6,537,249 | B2 | 3/2003 | Kriesell et al. |
| 6,539,286 | B1 | 3/2003 | Jiang |
| 6,569,115 | B1 | 5/2003 | Barker et al. |
| 6,595,956 | B1 | 7/2003 | Gross et al. |
| 6,656,158 | B2 | 12/2003 | Mahoney et al. |
| 6,699,218 | B2 | 3/2004 | Flaherty et al. |
| 6,723,072 | B2 | 4/2004 | Flaherty et al. |
| 6,740,059 | B2 | 5/2004 | Flaherty |
| 6,749,407 | B2 | 6/2004 | Xie et al. |
| 6,851,260 | B2 | 2/2005 | Mernoe |
| 6,883,778 | B1 | 4/2005 | Newton et al. |
| 7,018,360 | B2 | 3/2006 | Flaherty et al. |
| 7,104,275 | B2 | 9/2006 | Dille |
| 7,128,727 | B2 | 10/2006 | Flaherty et al. |
| 7,137,964 | B2 | 11/2006 | Flaherty |
| 7,160,272 | B1 | 1/2007 | Eyal et al. |
| 7,303,549 | B2 | 12/2007 | Flaherty |
| 7,771,392 | B2 | 8/2010 | De Polo et al. |
| 7,914,499 | B2 | 3/2011 | Gonnelli et al. |
| 7,951,114 | B2 | 5/2011 | Rush et al. |
| 8,267,921 | B2 | 9/2012 | Yodfat et al. |
| 8,382,703 | B1 | 2/2013 | Abdelaal |
| 8,499,913 | B2 | 8/2013 | Gunter |
| 8,905,995 | B2 | 12/2014 | Mernoe |
| 8,920,376 | B2 | 12/2014 | Caffey et al. |
| 8,939,935 | B2 | 1/2015 | OConnor et al. |
| 9,180,244 | B2 | 11/2015 | Anderson et al. |
| 9,192,716 | B2 | 11/2015 | Jugl et al. |
| 9,402,950 | B2 | 8/2016 | Dilanni et al. |
| 9,539,596 | B2 | 1/2017 | Ikushima |
| 10,441,723 | B2 | 10/2019 | Nazzaro |
| 10,695,485 | B2 | 6/2020 | Nazzaro |
| 2001/0016710 | A1 | 8/2001 | Nason et al. |
| 2001/0056258 | A1 | 12/2001 | Evans |
| 2002/0029018 | A1 | 3/2002 | Jeffrey |
| 2002/0032374 | A1 | 3/2002 | Holker et al. |
| 2002/0037221 | A1 | 3/2002 | Mastrangelo et al. |
| 2002/0173769 | A1 | 11/2002 | Gray et al. |
| 2002/0173830 | A1 | 11/2002 | Starkweather et al. |
| 2003/0040715 | A1 | 2/2003 | DAntonio et al. |
| 2003/0055380 | A1 | 3/2003 | Flaherty |
| 2003/0097092 | A1 | 5/2003 | Flaherty |
| 2003/0109827 | A1 | 6/2003 | Lavi et al. |

(56) References Cited

U.S. PATENT DOCUMENTS

| 2003/0163097 A1 | 8/2003 | Fleury et al. |
| 2003/0198558 A1 | 10/2003 | Nason et al. |
| 2003/0199825 A1 | 10/2003 | Flaherty |
| 2004/0010207 A1 | 1/2004 | Flaherty et al. |
| 2004/0064088 A1 | 4/2004 | Gorman et al. |
| 2004/0068224 A1 | 4/2004 | Couvillon, Jr. et al. |
| 2004/0069044 A1 | 4/2004 | Lavi et al. |
| 2004/0092865 A1 | 5/2004 | Flaherty et al. |
| 2004/0094733 A1 | 5/2004 | Hower et al. |
| 2004/0153032 A1 | 8/2004 | Garribotto et al. |
| 2005/0004529 A1 | 1/2005 | Veasey et al. |
| 2005/0020980 A1 | 1/2005 | Inoue et al. |
| 2005/0165363 A1 | 7/2005 | Judson et al. |
| 2005/0203461 A1 | 9/2005 | Flaherty et al. |
| 2005/0238507 A1 | 10/2005 | Dilanni et al. |
| 2005/0245878 A1 | 11/2005 | Mernoe et al. |
| 2005/0273059 A1 | 12/2005 | Mernoe |
| 2005/0277882 A1 | 12/2005 | Kriesel |
| 2006/0041229 A1 | 2/2006 | Garibotto et al. |
| 2006/0079765 A1 | 4/2006 | Neer et al. |
| 2006/0155210 A1 | 7/2006 | Beckman et al. |
| 2006/0173439 A1 | 8/2006 | Thorne et al. |
| 2006/0178633 A1 | 8/2006 | Garibotto et al. |
| 2006/0253085 A1 | 11/2006 | Geismar et al. |
| 2006/0282290 A1 | 12/2006 | Flaherty et al. |
| 2007/0005018 A1 | 1/2007 | Tekbuchava |
| 2007/0073236 A1 | 3/2007 | Merno et al. |
| 2007/0088271 A1 | 4/2007 | Richards |
| 2007/0118405 A1 | 5/2007 | Campbell et al. |
| 2007/0282269 A1 | 12/2007 | Carter et al. |
| 2008/0004515 A1 | 1/2008 | Jennewine |
| 2008/0051738 A1 | 2/2008 | Griffin |
| 2008/0114304 A1 | 5/2008 | Nalesso et al. |
| 2008/0172028 A1 | 7/2008 | Blomquist |
| 2008/0243211 A1 | 10/2008 | Cartwright et al. |
| 2008/0294040 A1 | 11/2008 | Mohiuddin et al. |
| 2009/0024083 A1 | 1/2009 | Kriesel et al. |
| 2009/0062767 A1 | 3/2009 | Van Antwerp et al. |
| 2009/0198215 A1 | 8/2009 | Chong et al. |
| 2009/0278875 A1 | 11/2009 | Holm et al. |
| 2009/0326472 A1 | 12/2009 | Carter et al. |
| 2010/0036326 A1 | 2/2010 | Matusch |
| 2010/0152658 A1 | 6/2010 | Hanson et al. |
| 2010/0168672 A1 | 7/2010 | Carr |
| 2010/0241066 A1 | 9/2010 | Hansen et al. |
| 2011/0054399 A1 | 3/2011 | Chong et al. |
| 2011/0073620 A1 | 3/2011 | Verrilli |
| 2011/0144586 A1 | 6/2011 | Michaud et al. |
| 2011/0180480 A1 | 7/2011 | Kloeffel et al. |
| 2011/0230833 A1 | 9/2011 | Landman et al. |
| 2012/0078161 A1 | 3/2012 | Masterson et al. |
| 2012/0172817 A1 | 7/2012 | Bruggemann et al. |
| 2012/0209207 A1 | 8/2012 | Gray et al. |
| 2013/0006213 A1 | 1/2013 | Arnitz et al. |
| 2013/0017099 A1 | 1/2013 | Genoud |
| 2013/0064701 A1 | 3/2013 | Konishi |
| 2013/0177455 A1 | 7/2013 | Kamen et al. |
| 2013/0178803 A1 | 7/2013 | Raab |
| 2013/0245545 A1 | 9/2013 | Arnold et al. |
| 2013/0267932 A1 | 10/2013 | Franke et al. |
| 2013/0296792 A1 | 11/2013 | Cabiri |
| 2014/0018730 A1 | 1/2014 | Muller-Pathle |
| 2014/0127048 A1 | 5/2014 | Dilanni et al. |
| 2014/0128839 A1 | 5/2014 | Dilanni et al. |
| 2014/0142508 A1 | 5/2014 | Dilanni et al. |
| 2014/0148784 A1 | 5/2014 | Anderson et al. |
| 2014/0171901 A1 | 6/2014 | Langsdorf et al. |
| 2015/0041498 A1 | 2/2015 | Kakiuchi et al. |
| 2015/0051487 A1 | 2/2015 | Uber et al. |
| 2015/0057613 A1 | 2/2015 | Clemente et al. |
| 2015/0064036 A1 | 3/2015 | Eberhard |
| 2015/0137017 A1 | 5/2015 | Ambrosina et al. |
| 2015/0202386 A1 | 7/2015 | Brady et al. |
| 2015/0290389 A1 | 10/2015 | Nessel |
| 2015/0297825 A1 | 10/2015 | Focht et al. |
| 2016/0008549 A1 | 1/2016 | Plumptre et al. |
| 2016/0025544 A1 | 1/2016 | Kamen |
| 2016/0055842 A1 | 2/2016 | Defranks et al. |
| 2016/0082242 A1 | 3/2016 | Burton et al. |
| 2016/0129190 A1 | 5/2016 | Haitsuka |
| 2016/0193423 A1 | 7/2016 | Bilton |
| 2016/0213851 A1 | 7/2016 | Weibel et al. |
| 2017/0021096 A1 | 1/2017 | Cole et al. |
| 2017/0021137 A1 | 1/2017 | Cole |
| 2017/0100541 A1 | 4/2017 | Constantineau et al. |
| 2017/0216516 A1 | 8/2017 | Dale |
| 2017/0239415 A1 | 8/2017 | Hwang et al. |
| 2017/0290975 A1 | 10/2017 | Barmaimon et al. |
| 2018/0021521 A1 | 1/2018 | Sanchez |
| 2018/0185579 A1 | 7/2018 | Joseph et al. |
| 2018/0313346 A1 | 11/2018 | Oakes |
| 2019/0192782 A1 | 6/2019 | Pedersen et al. |
| 2019/0365993 A1 | 12/2019 | Staub et al. |
| 2019/0366010 A1* | 12/2019 | Cardinali .......... A61M 5/31583 |
| 2020/0009315 A1 | 1/2020 | Brouet et al. |
| 2020/0345931 A1 | 11/2020 | Gray et al. |
| 2021/0236718 A1 | 8/2021 | Nagata et al. |

FOREIGN PATENT DOCUMENTS

| CN | 102498292 B | 7/2015 |
| CN | 204972511 U | 1/2016 |
| CN | 105764543 B | 7/2016 |
| CN | 206175149 U | 5/2017 |
| CN | 107096091 A | 8/2017 |
| CN | 108472441 A | 8/2018 |
| DE | 4200595 A1 | 7/1993 |
| DE | 19723648 C1 | 8/1998 |
| DE | 102005040344 A1 | 3/2007 |
| EP | 0454331 A1 | 10/1991 |
| EP | 0789146 A1 | 8/1997 |
| EP | 867196 A2 | 9/1998 |
| EP | 1065378 A2 | 1/2001 |
| EP | 1177802 A1 | 2/2002 |
| EP | 1403519 A1 | 3/2004 |
| EP | 2397181 A1 | 12/2011 |
| EP | 2468338 A1 | 6/2012 |
| EP | 2703024 A1 | 3/2014 |
| EP | 1874390 B1 | 10/2014 |
| EP | 2830499 A1 | 2/2015 |
| FR | 2096275 A5 | 2/1972 |
| FR | 2455269 A1 | 11/1980 |
| FR | 2507637 A1 | 12/1982 |
| FR | 2731475 A1 | 9/1996 |
| GB | 357139 A | 9/1931 |
| GB | 810488 A | 3/1959 |
| GB | 875034 A | 8/1961 |
| GB | 1204836 A | 9/1970 |
| GB | 2008806 A | 6/1979 |
| GB | 2077367 A | 12/1981 |
| GB | 2456681 A | 7/2009 |
| GB | 2549750 A | 11/2017 |
| IL | 46017 A | 11/1977 |
| JP | H03-141873 A | 6/1991 |
| JP | 06063133 A | 3/1994 |
| JP | H06296690 A | 10/1994 |
| JP | H08238324 A | 9/1996 |
| JP | 2003-531689 A | 10/2003 |
| JP | 2004247271 A | 9/2004 |
| JP | 2004274719 A | 9/2004 |
| JP | 2005188355 A | 7/2005 |
| JP | 2006159228 A | 6/2006 |
| JP | 6098988 B2 | 9/2006 |
| JP | 2006249130 A | 9/2006 |
| JP | 2009514580 A | 4/2009 |
| JP | 2015-519135 A | 7/2015 |
| JP | 2016-525182 A | 8/2016 |
| JP | 2017513577 A | 6/2017 |
| JP | 2020-526306 A | 8/2020 |
| NL | 1019126 C1 | 4/2003 |
| WO | 8101658 A1 | 6/1981 |
| WO | 8606796 A1 | 11/1986 |
| WO | 9320864 A1 | 10/1993 |
| WO | 9415660 A1 | 7/1994 |

(56) References Cited

FOREIGN PATENT DOCUMENTS

| WO | 9855073 | A1 | 12/1998 |
|----|---------|----|---------|
| WO | 9856293 | A1 | 12/1998 |
| WO | 9910040 | A1 | 3/1999 |
| WO | 9910049 | A1 | 3/1999 |
| WO | 9962576 | A1 | 12/1999 |
| WO | 0029047 | A1 | 5/2000 |
| WO | 0178812 | A1 | 10/2001 |
| WO | 0220073 | A2 | 3/2002 |
| WO | 0226282 | A2 | 4/2002 |
| WO | 2002076535 | A1 | 4/2002 |
| WO | 2003097133 | A1 | 4/2002 |
| WO | 02068823 | A1 | 9/2002 |
| WO | 2004032994 | A2 | 4/2004 |
| WO | 2004056412 | A2 | 7/2004 |
| WO | 2004110526 | A1 | 12/2004 |
| WO | 2007066152 | A2 | 6/2007 |
| WO | 2008133702 | A1 | 11/2008 |
| WO | 2009039203 | A2 | 3/2009 |
| WO | 2009141005 | A1 | 11/2009 |
| WO | 2010022069 | A2 | 2/2010 |
| WO | 2010077279 | A1 | 7/2010 |
| WO | 2010139793 | A1 | 12/2010 |
| WO | 2011010198 | A2 | 1/2011 |
| WO | 2011031458 | A1 | 3/2011 |
| WO | 2011069935 | A2 | 6/2011 |
| WO | 2011075042 | A1 | 6/2011 |
| WO | 2011133823 | A1 | 10/2011 |
| WO | 2012073032 | A1 | 6/2012 |
| WO | 2013050535 | A2 | 4/2013 |
| WO | 2013137893 | A1 | 9/2013 |
| WO | 2013149186 | A1 | 10/2013 |
| WO | 2014029416 | A1 | 2/2014 |
| WO | 2014149357 | A1 | 9/2014 |
| WO | 2014179774 | A1 | 11/2014 |
| WO | 2015032772 | A1 | 3/2015 |
| WO | 2015048791 | A1 | 4/2015 |
| WO | 2015081337 | A2 | 6/2015 |
| WO | 2015117854 | A1 | 8/2015 |
| WO | 2015167201 | A1 | 11/2015 |
| WO | 2015177082 | A1 | 11/2015 |
| WO | 2017148855 | A1 | 9/2017 |
| WO | 2017187177 | A1 | 11/2017 |
| WO | 2021016452 | A1 | 1/2021 |
| WO | 2021094045 | A1 | 5/2021 |

OTHER PUBLICATIONS

Lind et al. "Linear Motion Miniature Actuators." Paper presented at the 2nd Tampere International Conference on Machine Automation, Tampere, Finland (Sep. 1998).

Author Unknown "The Animas R-1000 Insulin Pump—Animas Corporation intends to exit the insulin pump businessand discontinue the manufacturing and sale of Animas® Vibe® and One Touch Ping® insulin bumps." [online], Dec. 1999 [retrieved on Jan. 8, 2019]. Retrieved from the Internet URL: http://www.animaspatientsupport.com/.

Author Unknown, CeramTec "Discover the Electro Ceramic Products CeramTec acquired from Morgan AdvancedMaterials" [online], Mar. 1, 2001 [retrieved on Jan. 8, 2019. Retrieved from the Internet URL: http://www.morgantechnicalceramics.com/.

Vaughan, M.E., "The Design, Fabrication, and Modeling of a Piezoelectric Linear Motor." Master's thesis, Virginia Polytechnic Institute and State University, VA. (2001).

Galante et al., "Design, Modeling, and Performance of a High Force Piezoelectric Inchworm Motor," Journal of Intelligent Material Systems and Structures, vol. 10, 962-972 (1999).

International Search Report and Written Opinion for International Application No. PCT/US2017/055054, mailed on Jan. 25, 2018, 13 pages.

International Search Report and Written Opinion for International Application No. PCT/US2018/045155, mailed on Oct. 15, 2018, 15 pages.

International Preliminary Report on Patentability for International Application No. PCT/US2017/034811 issued on Nov. 27, 2018, 10 pages.

International Preliminary Report on Patentability for International Patent Application No. PCT/US2017/046508, Feb. 12, 2019, 10 pages.

International Search Report and Written Opinion for International Application No. PCT/US2017/046508, mailed on Jan. 17, 2018, 14 pages.

International Search Report and Written Opinion for International Application No. PCT/US2017/046777, mailed on Dec. 13, 2017, 14 pages.

International Search Report and Written Opinion for International Application No. PCT/US2017/046737, mailed on Dec. 14, 2017, 11 pages.

International Search Report and Written Opinion for International Application No. PCT/US2017/034814, mailed on Oct. 11, 2017, 18 pages.

European Search Report and Written Opinion for the European Patent Application No. EP19177571, dated Oct. 30, 2019, 8 pages.

International Preliminary Report on Patentability for International Patent Application No. PCT/US2018/014351, dated Jul. 23, 2019, 7 pages.

International Preliminary Report on Patentability for International Patent Application No. PCT/US2017/046777, dated Feb. 19, 2019, 8 pages.

International Preliminary Report on Patentability for International Patent Application No. PCT/US2017/046737, dated Feb. 19, 2019, 8 pages.

International Preliminary Report on Patentability for International Patent Application No. PCT/US2017/055054, dated Apr. 9, 2019, 8 pages.

International Search Report and Written Opinion for Application No. PCT/US2017/034811, mailed Oct. 18, 2017, 15 pages.

EPO Search Report received in Application No. 13768938.6, dated Nov. 11, 2015, 8 pages.

International Search Report and Written Opinion for PCT Application No. PCT/US13/34674, mailed Aug. 6, 2013, 17 pages.

International Search Report and Written Opinion for International Application No. PCT/GB2007/004073, Jan. 31, 2008, 8 pages.

International Search Report and Written Opinion for International Patent Application No. PCT/US2019/063615, dated May 3, 2020, 17 pages.

International Preliminary Report on Patentability for International Patent Application No. PCT/US2018/045155, dated Feb. 14, 2020, 10 pages.

International Search Report and Written Opinion for International Patent Application No. PCT/US2019/035756, dated Jul. 31, 2019, 11 pages.

International Search Report and Written Opinion for PCT Application No. PCT/US2019/059854, mailed Aug. 26, 2020, 15 pages.

International Search Report and Written Opinion, Application No. PCT/US2022/016713, mailed Aug. 5, 2022, 19 bages.

International Search Report and Written Opinion for International Patent Application No. PCT/US2022/029012, mailed Aug. 19, 2022, 12 pages.

European Search Report and Written Opinion for European Patent Application No. EP20174878, dated Sep. 29, 2020, 8 pages.

Schott web-page image from Jul. 9, 2016, https://www.us.schott.com/pharmaceutical_packaging/english/products/cartridges.html.

International Search Report and Written Opinion for International Patent Application No. PCT/US2021/055581, dated Feb. 8, 2022, 19 pages.

International Search Report and Written Opinion for International Patent Application No. PCT/US2022/011356, dated Apr. 29, 2022, 19 pages.

International Search Report and Written Opinion for International Application No. PCT/US2022/078228, mailed on Jan. 9, 2023, 11 pages.

* cited by examiner

200

204a

204

230

210

204a

210

210

206

240

"B"

241

244

1500

DRIVE MECHANISM FOR POSITIVE DISPLACEMENT PUMPS

RELATED APPLICATIONS

This application claims the benefit of U.S. Provisional Patent Application No. 63/256,714, filed Oct. 18, 2021, the contents of which are incorporated herein by reference in their entirety.

BACKGROUND

Many conventional automatic drug delivery systems are well known, including, for example, wearable drug delivery devices of the type shown in FIG. 15. The drug delivery device 1500 can be designed to deliver any type of liquid drug to a user. In specific embodiments, the drug delivery device 1500 can be, for example, an OmniPod® drug delivery device manufactured by Insulet Corporation of Acton, Massachusetts. The drug delivery device 1500 can be a drug delivery device such as those described in U.S. Pat. Nos. 7,303,549, 7,137,964, or 6,740,059, each of which is incorporated herein by reference in its entirety.

Drug delivery device 1500 typically includes a positive displacement pump mechanism. Typically, the pump mechanism comprises a reservoir that stores the liquid drug. The liquid drug stored in the reservoir may be delivered to the user by expelling the drug from a reservoir using a driven plunger that longitudinally translates though the reservoir to force the liquid drug through a fluid port defined in the reservoir. The plunger may be longitudinally translated through the reservoir by, for example, a leadscrew or other type of linkage driven by a drive mechanism.

In wearable, on-body devices, it is desirable to keep the pump mechanism, as well as the overall drug delivery device 1500, as small as possible to minimize the impact to the wearer. Additionally, because such drug delivery devices are typically powered by an on-board battery, it is desirable to minimize the power required to operate the device.

In prior art drug delivery devices, the required angular motion/torque to drive the pump is provided by a ratcheting mechanism. The ratcheting mechanism may include, for example, two wires composed of a shape memory alloy (SMA), or a spring and one SMA wire, such as Nitinol, a metal hook, and ratchet wheels, where the SMA wires pull on the metal hook which pushes on the ratchet teeth and advances the pump to deliver a dose of the liquid drug. This type of ratcheting mechanism occupies a relatively large volume on the inside of one or more housings of the drug delivery device 1500 and may require a relatively large SMA wire force to operate the pump mechanism. Using an alternative drive mechanism with smaller form factor would therefore play a significant role in reducing the overall size of the drug delivery device. Further, a lower required SMA wire actuation force will reduce the overall energy required to operate the device. The reduced energy requirements may enable the use of a fewer number of batteries or different types of battery with a smaller form factor to operate the device, which will lead to further size reduction of the drug delivery device.

Therefore, it would be desirable to replace the prior art pump mechanism with a positive displacement pump mechanism having an improved drive mechanism for driving the plunger within the reservoir that does not require the large footprint of the prior art pump mechanism and that minimizes power consumption of the device.

Definitions

As used herein, the term "*liquid drug*" should be interpreted to include any drug in liquid form capable of being administered by a drug delivery device via a subcutaneous cannula, including, for example, insulin or co-formulations of two or more of GLP-1, pramlintide, and insulin.

SUMMARY

Embodiments of the invention disclosed herein include a novel drive mechanism for a positive displacement pump of the type use in wearable drug delivery devices. The drive mechanism provides measured, rotational motion that may be used with various linkage designs coupling the drive mechanism to a plunger disposed in a reservoir to provide longitudinal translation of the plunger through the reservoir.

Embodiments of this invention use a cylindrically-shaped slider element configured with a channel on a circumferential surface thereof. The channel defines a zig-zag-shaped track therethrough. One or more interface elements, which, in various exemplary embodiments, may be pegs or ball bearings, are engaged with the track, such that a back and forth longitudinal motion of the slider element along its longitudinal axis causes movement of the one or more interface elements along the track through the channel, thus providing a movement of the interface elements around the circumference of the slider element. The movement of the one or more interface elements through the channel imparts a rotational motion to a header element disposed co-axially with the slider element and connected to the one or more interface elements. The header element is in turn connected to a gear train, for example, a planetary gear box, which may be coupled to the plunger of the pump mechanism via a linkage or via another type of mechanism.

In a first embodiment, the channel defined in the circumferential surface of the slider element defines a single zig-zag-shaped track therethrough, such that longitudinal motion of the slider element along a longitudinal axis in a first direction, from a neutral position to a first position, and then back to the neutral position, causes the interface elements to move through the channel a first angular distance, and, as a result, causes the header element to be rotated the first angular distance.

In a second embodiment, the channel defined in the circumferential surface of the slider element defines two zig-zag-shaped tracks therethrough, such that longitudinal motion of the cylinder along a longitudinal axis in a first direction, from a neutral position to a first position, and then back to the neutral position, causes movement of the interface elements through the channel along the first track, causing the header element to rotate a first angular distance. Longitudinal motion of the slider element along the longitudinal axis in a second, opposite direction, from the neutral position to a second position, and then back to the neutral position, causes movement of the interface elements through the channel along the second track, causing the header element to rotate a second (different) angular distance. The movement of the header element the first and second angular distances enabled by the movement of the interface elements along the first and second tracks, respectively, through the channel, provides the ability to dispense different volumes of the liquid drug using the same motion to move the slider element. The motion of the slider element in either the first or second longitudinal directions may be provided via an actuator comprising, for example, one or more wires composed of a SMA linked to the slider element. The workings of the slider element and associated components is described in further detail below.

BRIEF DESCRIPTION OF THE DRAWINGS

In the drawings, like reference characters generally refer to the same parts throughout the different views. In the following description, various embodiments of the present invention are described with reference to the following drawings, in which.

DETAILED DESCRIPTION

This disclosure presents various systems, components and methods for moving a liquid drug from a liquid reservoir in a drug delivery device to a patient interface, such as a needle or cannula. The embodiments described herein provide one or more advantages over conventional, prior art systems, components and methods, namely, a smaller footprint and reduced energy consumption.

Various embodiments of the present invention include systems and methods for delivering a medication to a user using a drug delivery device (sometimes referred to herein as a "pod"), either autonomously, or in accordance with a wireless signal received from an electronic device. In various embodiments, the electronic device may be a user device comprising a smartphone, a smart watch, a smart necklace, a module attached to the drug delivery device, or any other type or sort of electronic device that may be worn or carried by or on the body of the user and that executes an algorithm that computes the times and dosages of delivery of the medication. For example, the user device may execute an "artificial-pancreas" algorithm that computes the times and dosages of delivery of insulin. The user device may also be in communication with a sensor, such as a glucose sensor, that collects data on a physical attribute or condition of the user, such as a glucose level. The sensor may be disposed in or on the body of the user and may be part of the drug delivery device or may be a separate device in system 100. Alternatively, the drug delivery device may be in communication with the sensor in lieu of or in addition to the communication between the sensor and the user device. The communication may be direct (if, e.g., the sensor is integrated with or otherwise a part of the drug delivery device) or remote/wireless (if, e.g., the sensor is disposed in a different housing than the drug delivery device). In these embodiments, the sensor and/or drug delivery device contain computing hardware (e.g., a processor, memory, firmware, etc.) that executes some or all of the algorithm that computes the times and dosages of delivery of the medication.

Figure 1:
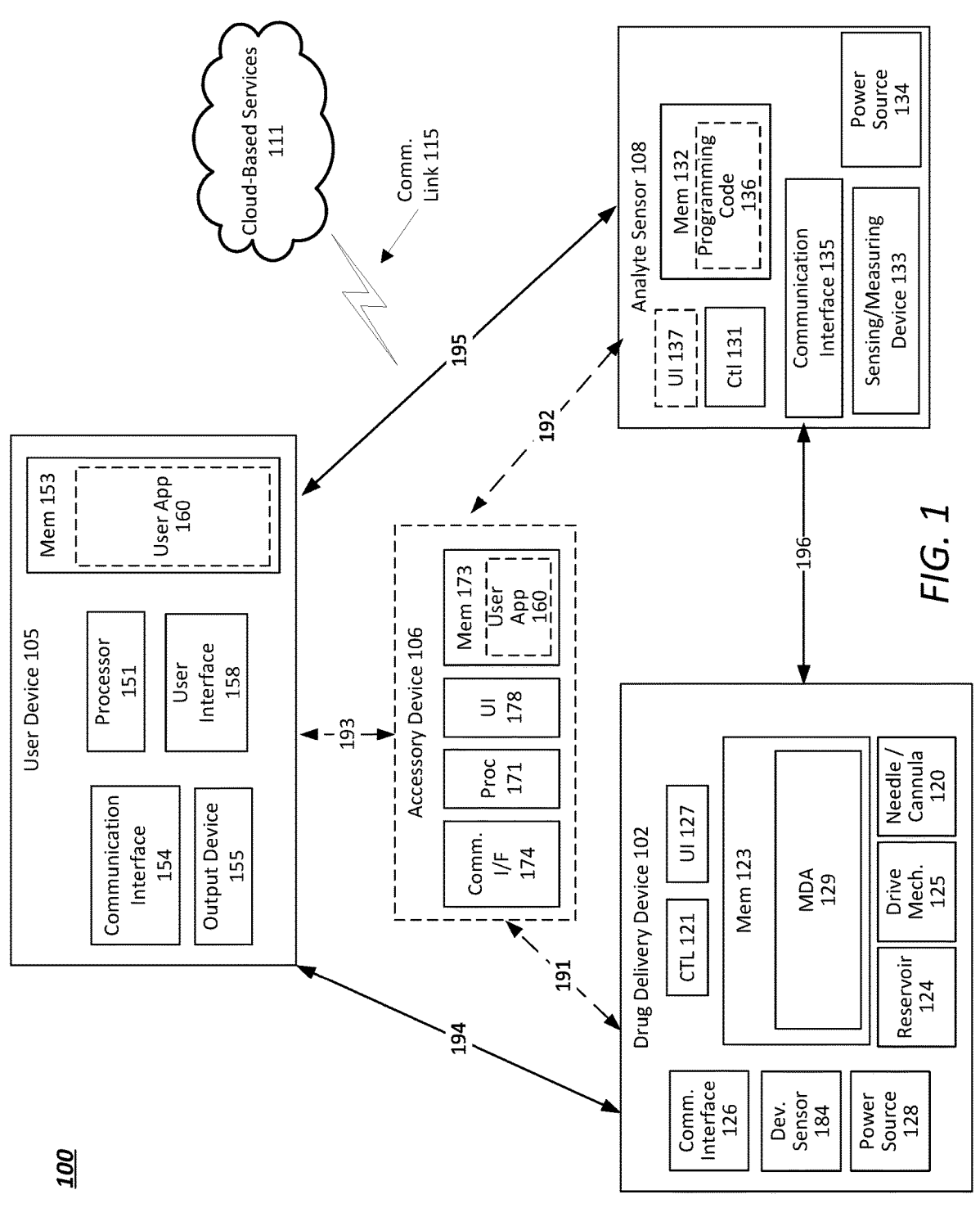
FIG. 1 illustrates a functional block diagram of an exemplary system suitable for implementing the systems and methods disclosed herein.

FIG. 1 illustrates a functional block diagram of an exemplary system suitable for implementing the systems and methods described herein. The automatic drug delivery system 100 may implement (and/or provide functionality for) a medication delivery algorithm, such as an artificial pancreas (AP) application, to govern or control automated delivery of a drug or medication, such as insulin, to a user (e.g., to maintain euglycemia—a normal level of glucose in the blood). The drug delivery system 100 may be an automated drug delivery system that may include a drug delivery device 102, which may be wearable, an analyte sensor 108, and a user device 105.

The system 100, in an optional example, may also include an accessory device 106, such as a smartwatch, a personal assistant device, or the like, which may communicate with the other components of system 100 via either a wired or wireless communication links 191-193.

The user device 105 may be a computing device such as a smartphone, a tablet, a personal diabetes management (PDM) device, a dedicated diabetes therapy management device, or the like. In an example, user device 105 may include a processor 151, device memory 153, a user interface 158, and a communication interface 154. The user device 105 may also contain analog and/or digital circuitry that may be implemented as a processor 151 for executing processes based on programming code stored in device memory 153, such as user application 160 to manage a user's blood glucose levels and for controlling the delivery of the drug, medication, or therapeutic agent to the user, as well for providing other functions, such as calculating carbohydrate-compensation dosage, a correction bolus dosage and the like as discussed below. The user device 105 may be used to program, adjust settings, and/or control operation of the wearable automatic drug delivery device 102 and/or the analyte sensor 103 as well as the optional smart accessory device 106.

The processor 151 may also be configured to execute programming code stored in device memory 153, such as the user app 160. The user app 160 may be a computer application that is operable to deliver a drug based on information received from the analyte sensor 103, the cloud-based services 111 and/or the user device 105 or optional accessory device 107. The memory 153 may also store programming code to, for example, operate the user interface 158 (e.g., a touchscreen device, a camera or the like), the communication interface 154 and the like. The processor 151, when executing user app 160, may be configured to implement indications and notifications related to meal ingestion, blood glucose measurements, and the like. The user interface 158 may be under the control of the processor 151 and be configured to present a graphical user interface that enables the input of a meal announcement, adjust setting selections and the like as described herein.

In a specific example, when the user app 160 is an artificial pancreas (AP) application, the processor 151 is also configured to execute a diabetes treatment plan (which may be stored in a memory) that is managed by user app 160. In addition to the functions mentioned above, when user app 160 is an AP application, it may further provide functionality to determine a carbohydrate-compensation dosage, a correction bolus dosage and determine a basal dosage according to a diabetes treatment plan. In addition, as an AP application, user app 160 provides functionality to output signals to the wearable automatic drug delivery device 102 via communications interface 154 to deliver the determined bolus and basal dosages.

The communication interface 154 may include one or more transceivers that operate according to one or more radio-frequency protocols. In one embodiment, the transceivers may comprise a cellular transceiver and a Bluetooth® transceiver. The communication interface 154 may be configured to receive and transmit signals containing information usable by user app 160.

User device 105 may be further provided with one or more output devices 155 which may be, for example, a speaker or a vibration transducer, to provide various signals to the user.

The wearable automatic drug delivery device 102, in the example system 100, may include a user interface 127, a controller 121, a drive mechanism 125, a communication interface 126, a memory 123, a power source/energy harvesting circuit 128, device sensors 184, and a reservoir 124. The wearable automatic drug delivery device 102 may be configured to perform and execute processes required to deliver doses of the medication to the user without input from the user device 105 or the optional accessory device 106. As explained in more detail, the controller 121 may be operable, for example, to determine an amount of insulin to be delivered, IOB, insulin remaining, and the like, based on an input from the analyte sensor 108.

The memory 123 may store programming code executable by the controller 121. The programming code, for example, may enable the controller 121 to control the delivery of medication from the reservoir 124 and control the administering of doses of medication based on signals from the medication delivery algorithm (MDA) 129 or, external devices, if the MDA 129 is configured to implement the external control signals.

The reservoir 124 may be configured to store drugs, medications or therapeutic agents suitable for automated delivery, such as insulin, GLP-1, pramlintide, co-formulations of insulin and GLP-1 or pramlintide, morphine, blood pressure medicines, chemotherapy drugs, fertility drugs or the like.

The device sensors 184 may include one or more of a pressure sensor, a power sensor, or the like that are communicatively coupled to the controller 121 and provide various signals. For example, a pressure sensor may be configured to provide an indication of the fluid pressure detected in a fluid pathway between a needle or cannula inserted in a user and the reservoir 124. The pressure sensor may be coupled to or integral with a needle/cannula insertion component (which may be part of the drive mechanism 125) or the like. In an example, the controller 121 or a processor, such as 151, may be operable to determine that a rate of drug infusion based on the indication of the fluid pressure. The rate of drug infusion may be compared to an infusion rate threshold, and the comparison result may be usable in determining an amount of insulin onboard (IOB) or a total daily insulin (TDI) amount.

In an example, the wearable automatic drug delivery device 102 includes a communication interface 126, which may be a transceiver that operates according to one or more radio-frequency protocols, such as Bluetooth, Wi-Fi, near-field communication, cellular, or the like. The controller 121 may, for example, communicate with user device 105 and an analyte sensor 108 via the communication interface 126.

The wearable automatic drug delivery device 102 may be attached to the body of a user, such as a patient or diabetic, at an attachment location and may deliver any therapeutic agent, including any drug or medicine as described above, to a user at or around the attachment location. A surface of the wearable automatic drug delivery device 102 may include an adhesive to facilitate attachment to the skin of a user.

The wearable automatic drug delivery device 102 may, for example, include a reservoir 124 for storing the drug, a needle or cannula 120 for delivering the drug into the body of the user (which may be done subcutaneously, intraperitoneally, or intravenously), and a drive mechanism 125 for transferring the drug from the reservoir 124 through a needle or cannula and into the user. The drive mechanism 125 may be fluidly coupled to reservoir 124, and communicatively coupled to the controller 121. Needle or cannula 120 may further comprise a needle/cannula insertion mechanism (not shown) which may be integral with drug delivery device 102 or attachable thereto.

The wearable automatic drug delivery device 102 may further include a power source 128, such as a battery, a piezoelectric device, an energy harvesting device, or the like, for supplying electrical power to the drive mechanism 125 and/or other components (such as the controller 121, memory 123, and the communication interface 126) of the wearable automatic drug delivery device 102.

In some examples, the wearable automatic drug delivery device 102 and/or the user device 105 may include a user interface 158, and an output device 155, such as a keypad, a touchscreen display, levers, light-emitting diodes, buttons on a housing of the drug delivery device 101, a microphone, a camera, a speaker, a display, or the like, that is configured to allow a user to enter information and allow the user device 105 to output information for presentation to the user (e.g., alarm signals or the like). The user interface 158 may provide inputs, such as a voice input, a gesture (e.g., hand or facial) input to a camera, swipes to a touchscreen, or the like, to processor 151 which the user app 160 interprets.

When configured to communicate with an external device, such as the user device 105 or the analyte sensor 108, the wearable automatic drug delivery device 102 may receive signals over the wired or wireless link 194 from the user device 105 or from the analyte sensor 108. The controller 121 of the wearable automatic drug delivery device 102 may receive and process the signals from the respective external devices as well as implementing delivery of a drug to the user according to a diabetes treatment plan or other drug delivery regimen.

In an operational example, the processor 121, when executing user app 160, may output a control signal operable to actuate the drive mechanism 125 to deliver a carbohydrate-compensation dosage of insulin, a correction bolus, a revised basal dosage or the like.

The accessory device 107 may be, for example, an Apple Watch®, other wearable smart device, including eyeglasses, smart jewelry, a global positioning system-enabled wearable, a wearable fitness device, smart clothing, or the like. Similar to user device 105, the accessory device 107 may also be configured to perform various functions including controlling the wearable automatic drug delivery device 102. For example, the accessory device 107 may include a communication interface 174, a processor 171, a user interface 178 and a memory 173. The user interface 178 may be a graphical user interface presented on a touchscreen display of the smart accessory device 107. The memory 173 may store programming code to operate different functions of the smart accessory device 107 as well as an instance of the user app 160, or a pared-down version of user app 160 with reduced functionality.

The analyte sensor 108 may include a controller 131, a memory 132, a sensing/measuring device 133, an optional user interface 137, a power source/energy harvesting circuitry 134, and a communication interface 135. The analyte sensor 108 may be communicatively coupled to the processor 151 of the management device 105 or controller 121 of the wearable automatic drug delivery device 102. The memory 132 may be configured to store information and programming code 136.

The analyte sensor 108 may be configured to detect multiple different analytes, such as glucose, lactate, ketones, uric acid, sodium, potassium, alcohol levels or the like, and output results of the detections, such as measurement values or the like. The analyte sensor 108 may, in an exemplary embodiment, be configured to measure a blood glucose value at a predetermined time interval, such as every 5 minutes, every 1 minute, or the like. The communication interface 135 of analyte sensor 108 may have circuitry that operates as a transceiver for communicating the measured blood glucose values to the user device 105 over a wireless link 195 or with wearable automatic drug delivery device 102 over the wireless communication link 108. While referred to herein as an analyte sensor 108, the sensing/measuring device 133 of the analyte sensor 108 may include one or more additional sensing elements, such as a glucose measurement element, a heart rate monitor, a pressure sensor, or the like. The controller 131 may include discrete, specialized logic and/or components, an application-specific integrated circuit, a microcontroller or processor that executes software instructions, firmware, programming instructions stored in memory (such as memory 132), or any combination thereof Similar to the controller 121 of drug delivery device 102, the controller 131 of the analyte sensor 108 may be operable to perform many functions. For example, the controller 131 may be configured by programming code 136 to manage the collection and analysis of data detected by the sensing and measuring device 133.

Although the analyte sensor 108 is depicted in FIG. 1 as separate from the wearable automatic drug delivery device 102, in various examples, the analyte sensor 108 and wearable automatic drug delivery device 102 may be incorporated into the same unit. That is, in various examples, the analyte sensor 108 may be a part of and integral with the wearable automatic drug delivery device 102 and contained within the same housing as the wearable automatic drug delivery device 102 or an attachable housing thereto. In such an example configuration, the controller 121 may be able to implement the functions required for the proper delivery of the medication alone without any external inputs from user device 105, the cloud-based services 111, another sensor (not shown), the optional accessory device 107, or the like.

The communication link 115 that couples the cloud-based services 111 to the respective devices 102, 105, 106, 108 of system 100 may be a cellular link, a Wi-Fi link, a Bluetooth link, or a combination thereof. Services provided by cloud-based services 111 may include data storage that stores data, which may be de-personalized, such as blood glucose measurement values, historical IOB or TDI, prior carbohydrate-compensation dosage, and other forms of data. In addition, the cloud-based services 111 may process the anonymized data from multiple users to provide generalized information related to TDI, insulin sensitivity, IOB and the like.

The wireless communication links 191-196 may be any type of wireless link operating using known wireless communication standards or proprietary standards. As an example, the wireless communication links 191-196 may provide communication links based on Bluetooth®, Zigbee®, Wi-Fi, a near-field communication standard, a cellular standard, or any other wireless protocol via the respective communication interfaces 154, 174, 126 and 135.

The user app 160 (or MDA 129) may provide periodic insulin micro-boluses based upon past glucose measurements and/or a predicted glucose over a prediction horizon (e.g., 60 minutes). Optimal post-prandial control may require the user to give meal boluses in the same manner as current pump therapy, but normal operation of the user app 160 will compensate for missed meal boluses and mitigate prolonged hyperglycemia. The user app 160 uses a control-to-target strategy that attempts to achieve and maintain a set target glucose value, thereby reducing the duration of prolonged hyperglycemia and hypoglycemia.

The user application 160 implements a graphical user interface that is the primary interface with the user and is used to start and stop a wearable drug delivery device 102, program basal and bolus calculator settings for manual mode as well as program settings specific for automated mode (hybrid closed-loop or closed-loop).

In manual mode, user app 160 will deliver insulin at programmed basal rates and bolus amounts with the option to set temporary basal profiles. The controller 121 will also have the ability to function as a sensor-augmented pump in manual mode, using sensor glucose data provided by the analyte sensor 108 to populate the bolus calculator.

In automated mode, the user app 160 supports the use of multiple target blood glucose values. For example, in one embodiment, target blood glucose values can range from 110-150 mg/dL, in 10 mg/dL increments, in 5 mg/dL increments, or other increments, but preferably 10 mg/dL increments. The experience for the user will reflect current setup flows whereby the healthcare provider assists the user to program basal rates, glucose targets and bolus calculator settings. These in turn will inform the user app 160 for insulin dosing parameters. The insulin dosing parameters will be adapted over time based on the total daily insulin (TDI) delivered during each use of drug delivery device 102. A temporary hypoglycemia protection mode may be implemented by the user for various time durations in automated mode. With hypoglycemia protection mode, the algorithm reduces insulin delivery and is intended for use over temporary durations when insulin sensitivity is expected to be higher, such as during exercise.

User app 160, allows the use of large text, graphics, and on-screen instructions to prompt the user through the set-up processes and the use of system 100. It will also be used to program the user's custom basal insulin delivery profile, check the status, of drug delivery device 102, initiate bolus doses of insulin, make changes to a patient's insulin delivery profile, handle system alerts and alarms, and allow the user to switch between automated mode and manual mode.

In some embodiments, user device 105 and the analyte sensor 108 may not communicate directly with one another. Instead, data (e.g., blood glucose readings) from analyte sensor may be communicated to drug delivery device 102 via link 196 and then relayed to user device 105 via link 194. In some embodiments, to enable communication between analyte sensor 108 and user device 102, the serial number of the analyte sensor must be entered into user app 160.

User app 160 may provide the ability to calculate a suggested bolus dose through the use of a bolus calculator. The bolus calculator is provided as a convenience to the user to aid in determining the suggested bolus dose based on ingested carbohydrates, most-recent blood glucose readings (or a blood glucose reading if using fingerstick), programmable correction factor, insulin to carbohydrate ratio, target glucose value and insulin on board (IOB). IOB is estimated by user app 160 taking into account any manual bolus and insulin delivered by the algorithm.

Software related implementations of the techniques described herein may include, but are not limited to, firmware, application specific software, or any other type of computer readable instructions that may be executed by one or more processors. The computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

In primary embodiments of the invention, the positive displacement pump comprises a reservoir having two ends, such as an open and a closed end, having a plunger disposed in one end, such as the open end, a drive mechanism and a linkage coupling the drive mechanism to the plunger. Movement of the drive mechanism causes the plunger to linearly translate within the reservoir toward the closed end, thereby expelling the liquid drug to the patient interface via a fluid port defined in the closed end of the reservoir.

Figure 2:
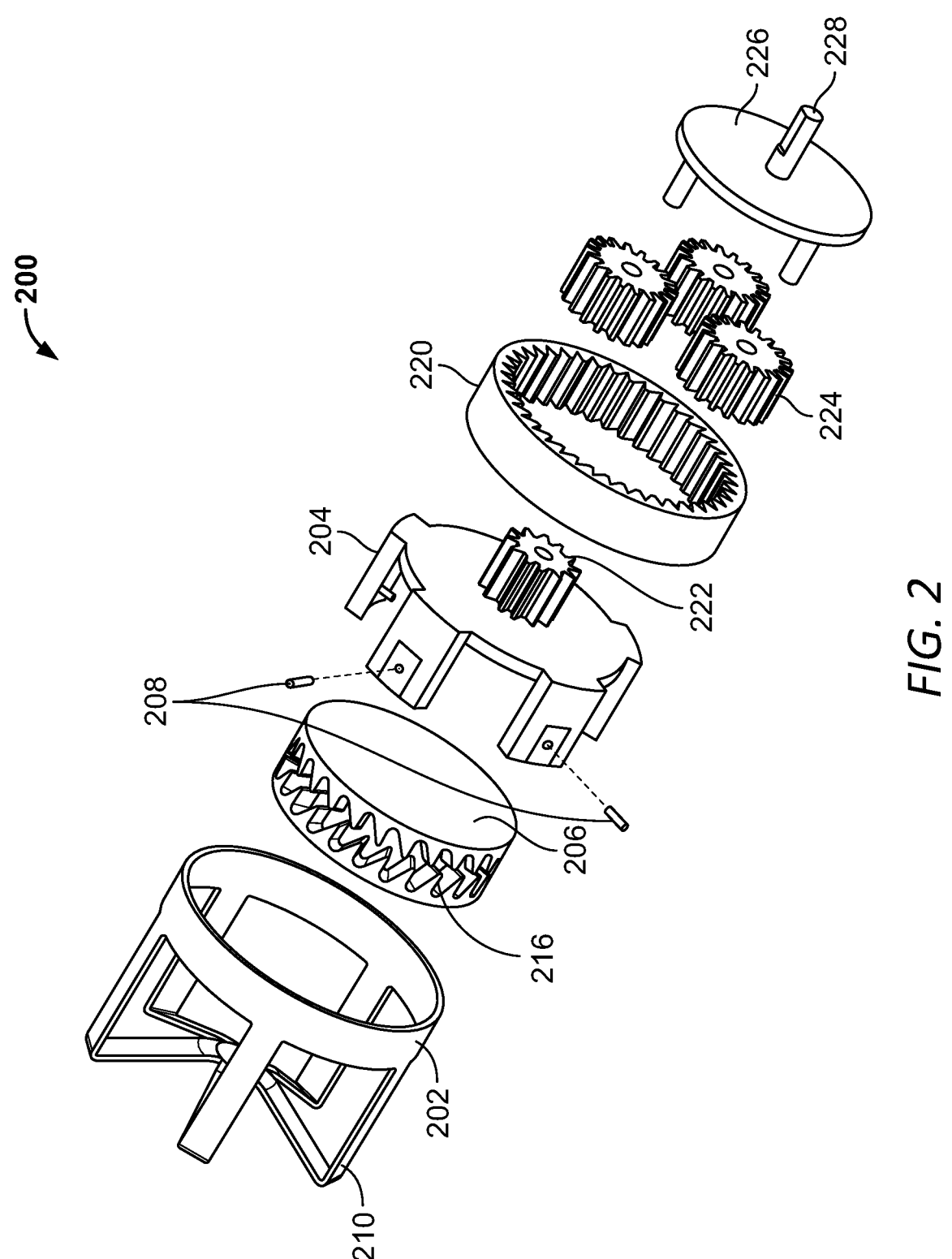
FIG. 2 is an exploded view of the drive mechanism of a first embodiment of the invention.

A first embodiment of the drive mechanism is described herein and is shown in exploded view in FIG. 2. The device comprises a housing 202 having integrated spring 210, though spring 210 may be fashioned in a non-physically integrated manner. Slider element 206 is generally cylindrically-shaped having channel 216 defined on the circumferential surface thereof. A zig-zag-shaped track is defined in channel 216. Header element 204 is disposed co-axially with slider element 206 and has a plurality of tabs 204a extending from a main body portion, the tabs 204a which overlap portions of channel 216 on slider element 206. In exemplary embodiments, header element 204 and slider element 206 may be fabricated using an injection molding process and may be composed of, for example, Polycarbonate or Acetal (polyoxymethylene or POM). In other exemplary embodiments, slider element 206 may be configured with stamped sheet metal covering the circumferential surface thereof and defining channel 216. Lubrication may be provided between header element 204 and slider element 206 to reduce friction or, alternatively, header element 204 and slider element 206 may be composed of a lubricated plastic resin. Additionally or alternatively, pegs 208 may be allowed to rotate along their longitudinal axis as they move or roll along sloped surfaces in channel 216. Allowing pegs 208 to rotate as they move may reduce the force required to push or pull slider element 206 in either direction. This and other features may be implemented in any of the embodiments described herein.

To coordinate the movement between header element 204 and slider element 206, a plurality of interface elements are disposed therebetween. In the primary embodiment, the interface elements comprise a plurality of pegs 208 extending through holes defined in the tabs 204a of header element 204 and into channel 216. In exemplary embodiments, pegs 208 may be composed of stainless steel or any other metal which provides the required strength, considering that pegs 208 may be of relatively small diameter.

Once slider element 206 and header element 204 are arranged within housing 202, a back-and-forth longitudinal motion of slider element 206 along a longitudinal axis thereof causes pegs 208 to translate in a zig-zag manner along the zig-zag-shaped track defined in channel 216, thereby causing rotation of header element 204 a predetermined angular distance about the coaxial axis of slider element 206 and header element 204.

Figure 3:
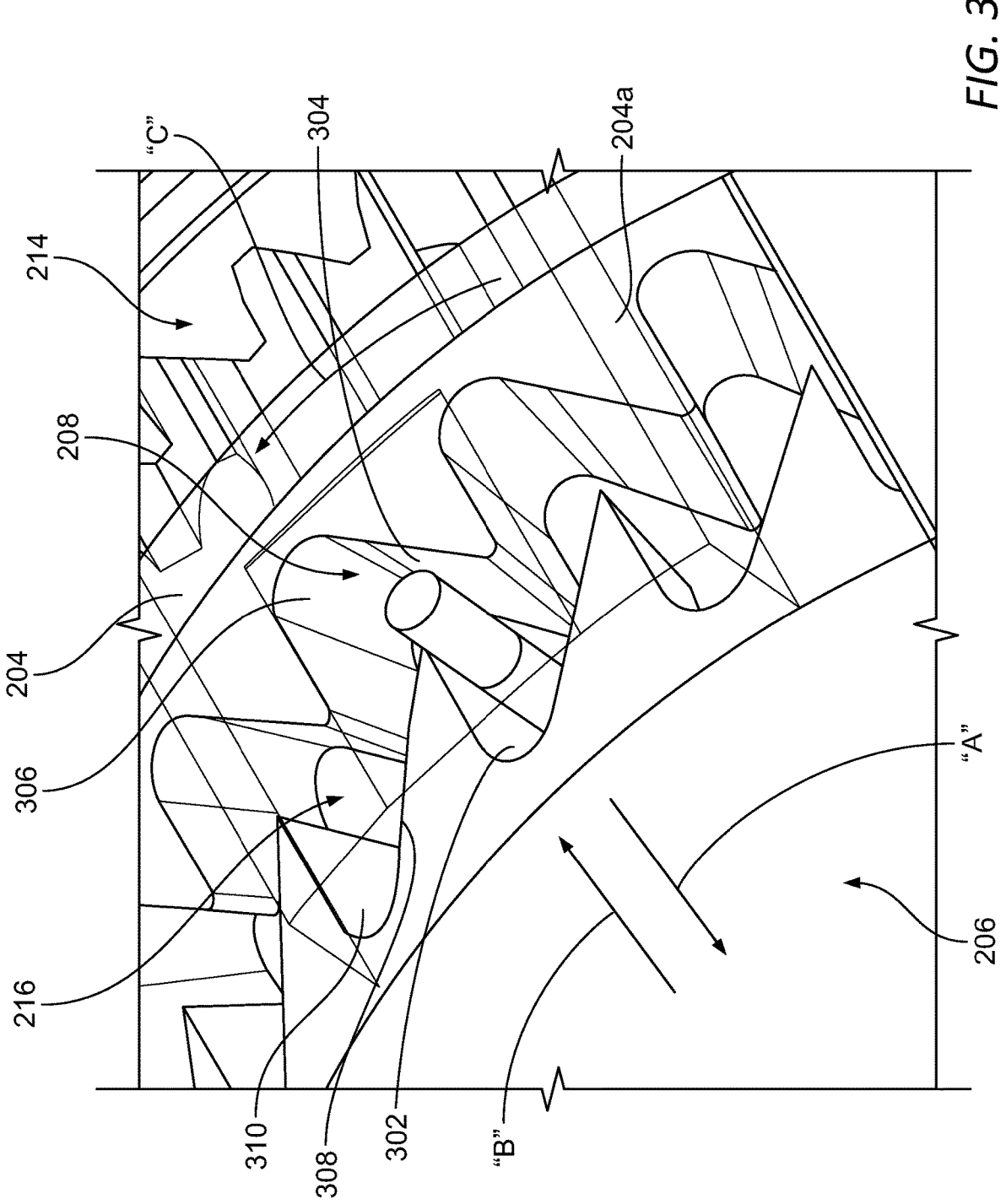
FIG. 3 is a close-up view of the zig-zag-shaped track of the first embodiment of the invention.

FIG. 3 shows a close-up view of slider element 206 having peg 208 disposed in channel 216. As can be seen, when peg 208 is located in concave section 302 of the zig-zag-shaped track, longitudinal motion of slider element 206 in direction "A" will cause peg 208 to come in contact with sloped section 304 of the zig-zag-shaped track, thereby forcing rotation of header element 204 in direction "C" until slider element 206 reaches a first position and peg 208 comes into contact with concave section 306 of the zig-zag-shaped track. At this point, longitudinal movement of slider element 206 in direction "B" as it returns to the neutral position, will cause peg 208 to come into contact with sloped section 308 of the zig-zag-shaped track, causing further rotation of header element 204 in direction "C", until peg 208 reaches concave portion 310 of the zig-zag-shaped track, when slider element 206 reaches the neutral position. The repeated back-and-forth motion in alternating in directions "A" and "B" of slider element 206, between the neutral position and the first position, causes header element 204 to rotate within housing 202 by virtue of movement of pegs 208 along the zig-zag-shaped track defined in channel 216. Note that, while FIG. 3 shows only one peg, in practice, multiple pegs 208 may extend from multiple tabs 204*a* of header element 204 into channel 216. Moreover, in this embodiment, slider element 206 does not rotate, but header element 204 does rotate; in an alternative embodiment, slider element 206 could rotate while header element 204 does not rotate.

Returning to FIG. 2, header element 204 is preferably coupled to a gear train to provide fine control of the rotation of output shaft 228. In one embodiment of the invention, the gear train may be a planetary gear system, as shown in FIG. 2. In other embodiments, other types of gear trains may be used, for example, a harmonic gear train or a set of interacting spur gears. In the case where a planetary gear system is used, header element 204 may define thereon sun gear 222 which will drive planet gears 224 within stationary ring gear 220. Carrier 226 is preferably coupled directly to planet gears 224 and defines output shaft 228 which may be coupled to a linkage (not shown) or other mechanism, which, in turn, is coupled to the plunger within the reservoir of the pump mechanism.

Figure 4:
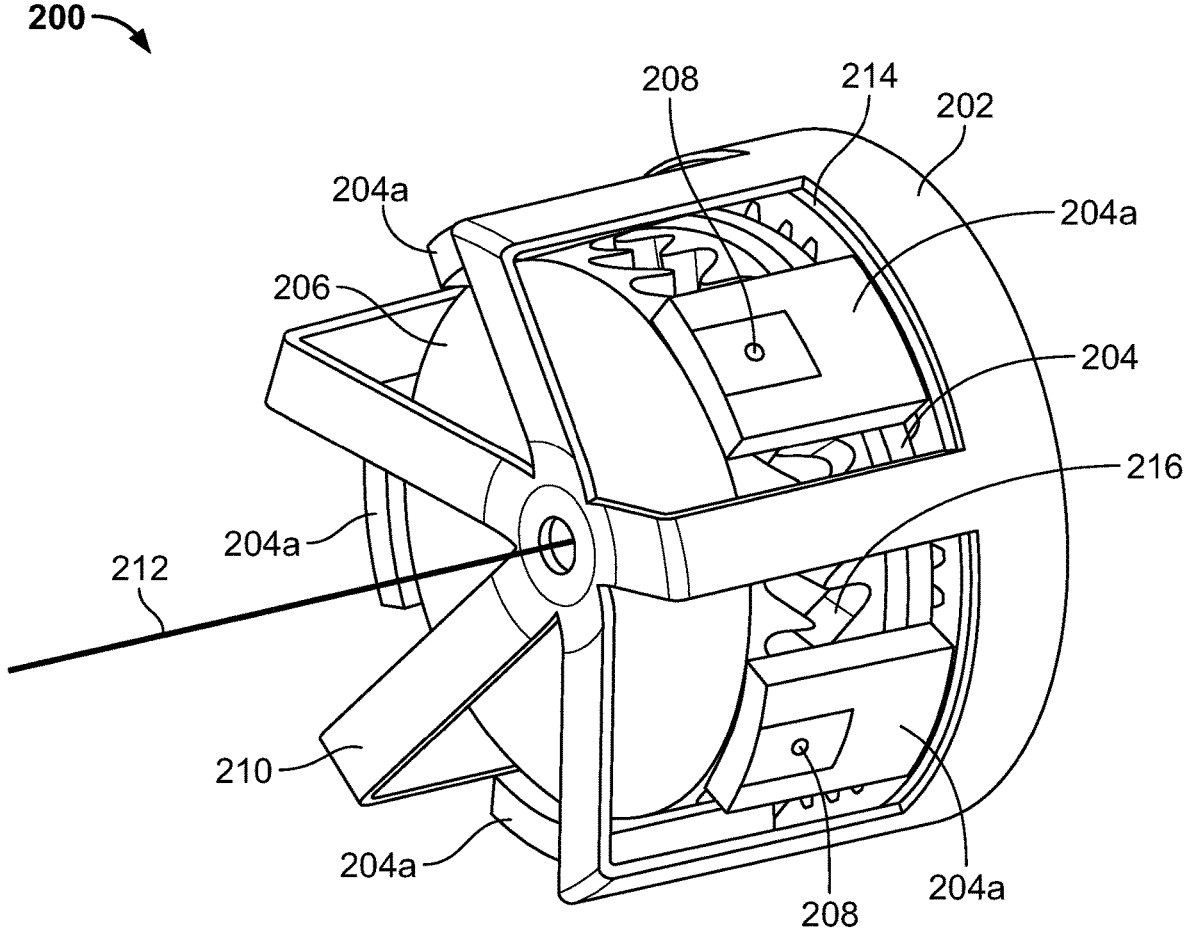
FIG. 4 is a perspective view of the first embodiment of the invention, showing the drive mechanism in a no-load configuration, with the slider element in the neutral position.
Figure 5:
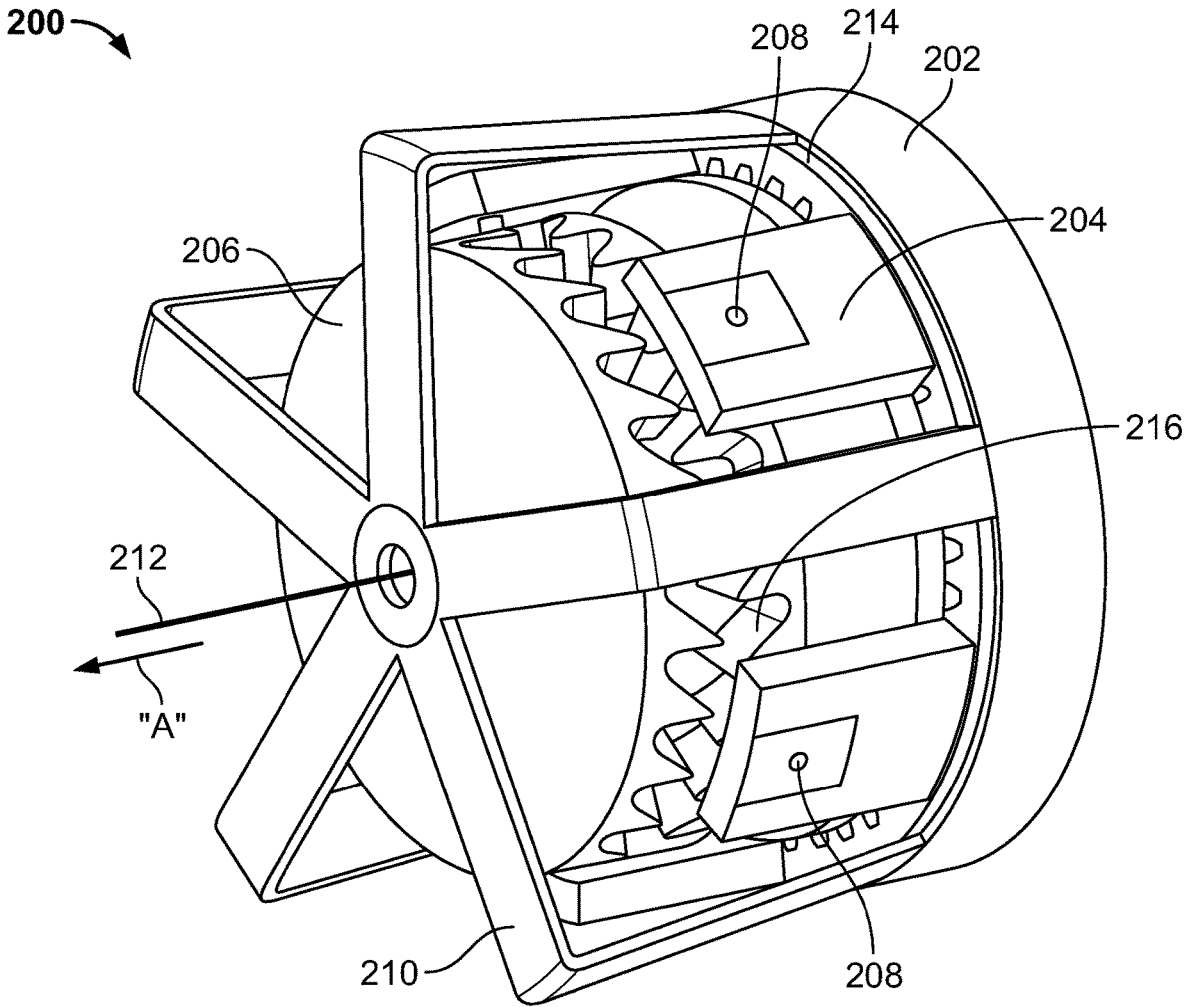
FIG. 5 is a perspective view of the first embodiment of the invention showing the drive mechanism in a loaded configuration, wherein the slider element has moved from the neutral position to a first position.

FIG. 4 shows drive mechanism 200 in its no-load (i.e., resting) configuration with slider element 206 in the neutral position. In one embodiment, the longitudinal motion of slider element 206 along its longitudinal axis in the first direction may be accomplished by connection to a wire 212 composed of a shape memory alloy (an SMA), which is preferably connected to a center point of cylindrically-shaped slider element 206. An application of a voltage to SMA wire 212 causes the contraction of SMA wire 212 so as to pull slider element 206 in direction "A" shown in FIG. 3, toward the first position. As shown in FIG. 5, movement of slider element 206 in direction "A" via contraction of SMA wire 212 will cause a tension on spring 210. When SMA wire 212 is relaxed and returns to its no-load state, spring 210 will compress, thereby pushing slider element 206 in direction "B" to return it to the neutral position shown in FIG. 4. In other embodiments of the invention, other means may be used to move slider element 206 in direction "A". For example, a solenoid could be used for this purpose.

Figure 6:
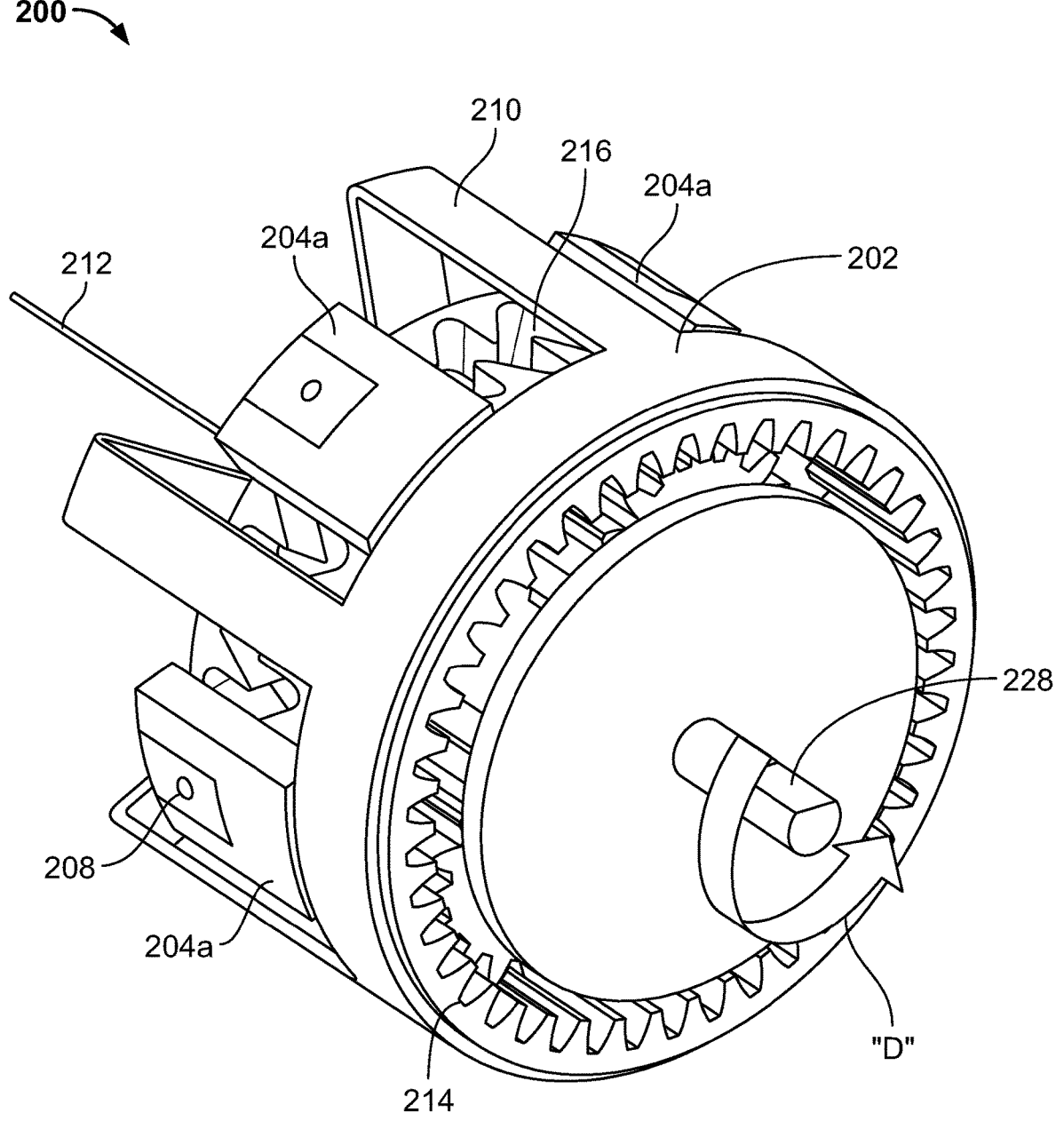
FIG. 6 is a perspective view of a first embodiment of the invention showing the resulting rotational motion of the output shaft produced by the back-and-forth motion of the slider element.

FIG. 6 is a perspective view of a completely assembled version of drive mechanism 200 shown from the opposite side, showing rotation of output shaft 228 in direction "D". Note that the use of the planetary gears will cause output shaft 228 to rotate in a direction opposite the direction of rotation of header element 204, which rotates in direction "C" shown in FIG. 3. The use of other types of gear trains may cause output shaft 220 to rotate in the same direction as header element 204.

Figures 7A, 7B:
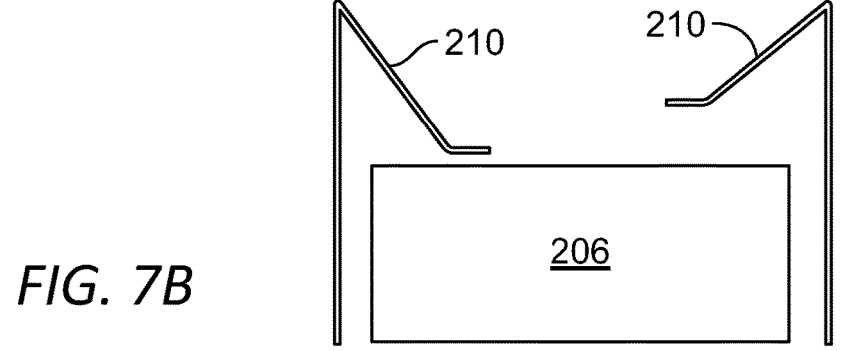
FIG. 7A shows an alternate implementation of the first embodiment of the invention utilizing a different type of spring mechanism.
FIG. 7B shows a side schematic view of a variation of the spring mechanism with offset legs.

FIG. 7A shows a variation of the first embodiment in which slider element 206 defines a proud cylindrical protrusion 230 on the surface adjacent spring mechanism 210, such that the legs of spring mechanism 210 engage the circumferential surface of protrusion 230. In this embodiment, the legs of spring 210 may engage protrusion 230 at different depths, as shown in FIG. 7B, so as to provide sequential engagement of the spring legs during an actuation cycle and to provide better control of the spring load profile. For example, the legs of spring 210 could be adjusted to provide extra stiffness at the end of a cycle.

Figure 8:
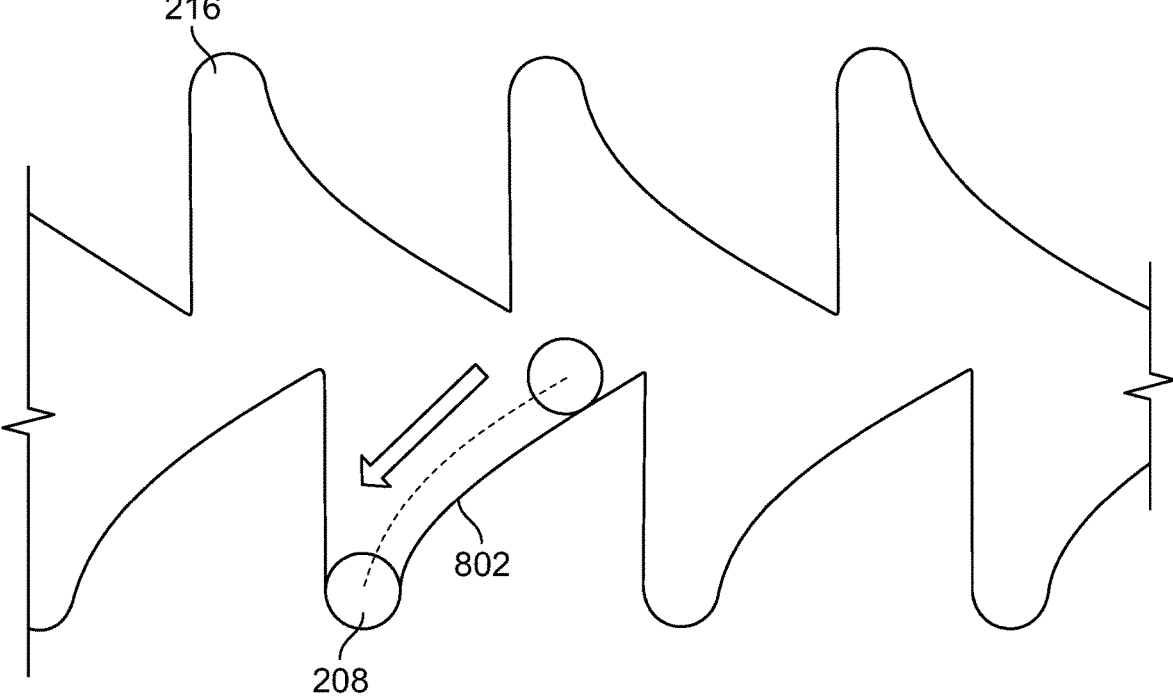
FIG. 8 is a schematic view of an alternate embodiment of the zig-zag track, showing the track having nonlinear sloped surfaces which allow better tuning of the load profile applied to the SMA wire and the output torque applied to the pump. Such surfaces could be employed in the first or second embodiments described herein.

FIG. 8 shows yet another variation of a first embodiment of the invention in which the sloped portions of the opposing walls, for example, 304 and 308, of the zig-zag-shaped track defined in channel 216 are provided with a curved profile

802 as opposed to the linear profile shown in FIG. 3. A similar sloped profile could be used in the second embodiment discussed herein. The curved profile 802 allows improved tuning of the load profile applied to the SMA wire 212 and the output torque applied to the pump. The example having a curved profile shown in FIG. 8 reduces the required force provided by SMA wire 212 at the end of the cycle. This is helpful because, in general, the SMA wire 212 is mechanically weakest at the end of the cycle. Other profiles may be used in place of curved profile 802, as long as the zig-zag motion of the pegs 208 within channel 216 can be maintained by the back-and-forth motion of slider element 206.

Figure 9:
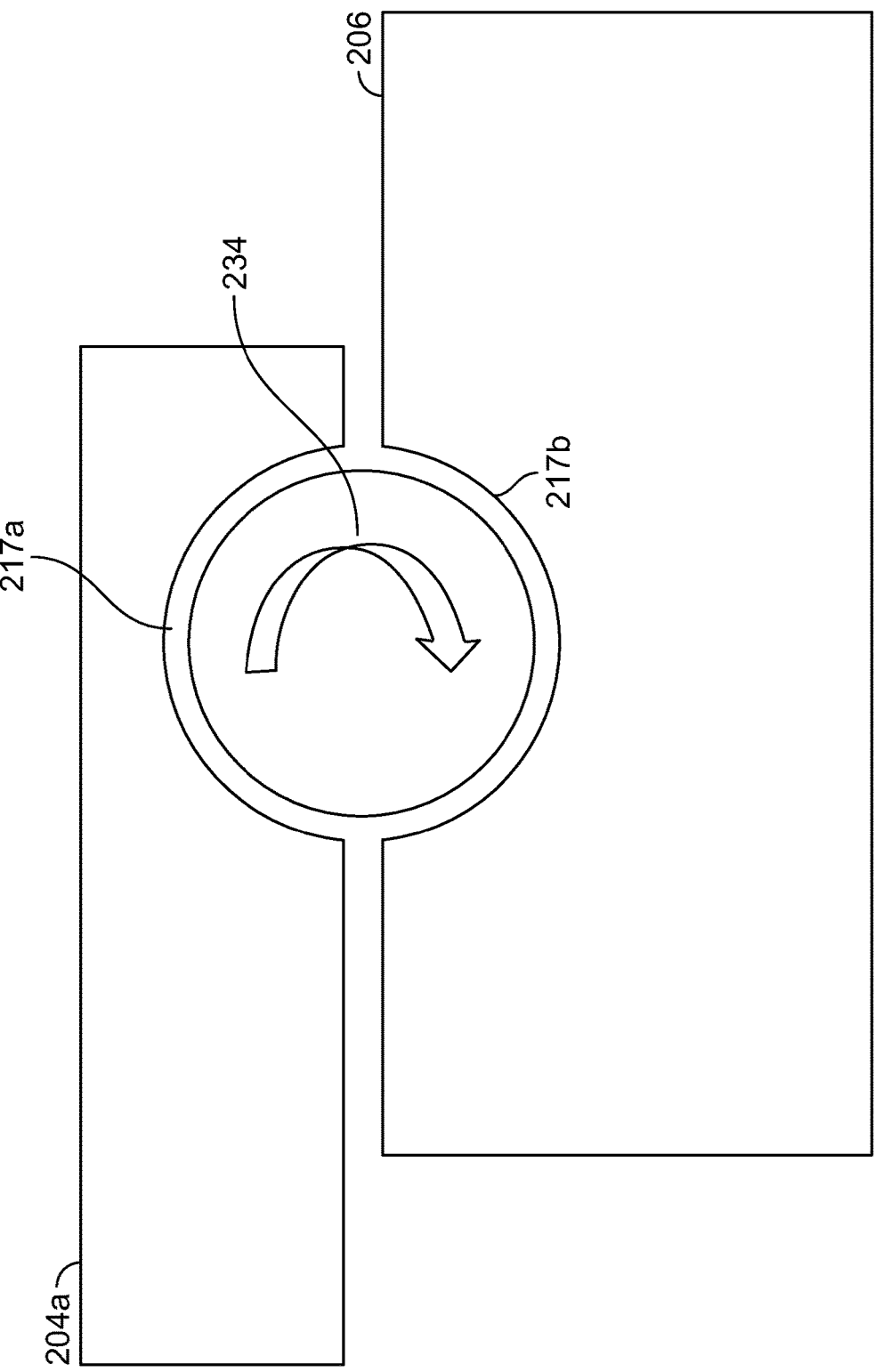
FIG. 9 is a block diagram of a second implementation of the first embodiment utilizing a ball bearing between the header element and the slider element as opposed to the pegs of the primary embodiment.

FIG. 9 shows an alternate embodiment of the invention in which the interface elements comprise ball bearings 234. The use of ball bearings 234 in lieu of pegs 208 of the primary embodiment is likely to reduce friction, and, thus, the energy required to angularly displace header element 204. In this embodiment, channel 216 in slider element 206 is made much shallower, becoming groove 217*b* having a semicircular cross-sectional shape, as shown in FIG. 9. In addition, each tab 204*a* of header element 204 is configured with a substantially hemispherically-shaped depression 217*a* therein, in which ball bearing 234 is partially disposed. The diameter of the semicircular groove 217*b* should be just slightly larger than the diameter of ball bearing 234, while ball bearing 234 should fit snugly into hemispherically-shaped depression 217*a*. One or more of tabs 204*a* defined on header element 204 may be configured with a hemispherical-shaped depression 217*a* and a ball bearing 234. To further reduce friction, it is desirable that tabs 204*a* of header element 204 and slider element 206 do not touch each other. In exemplary embodiments, ball bearings 234 may be composed of carbon chromium steel.

Figure 10:
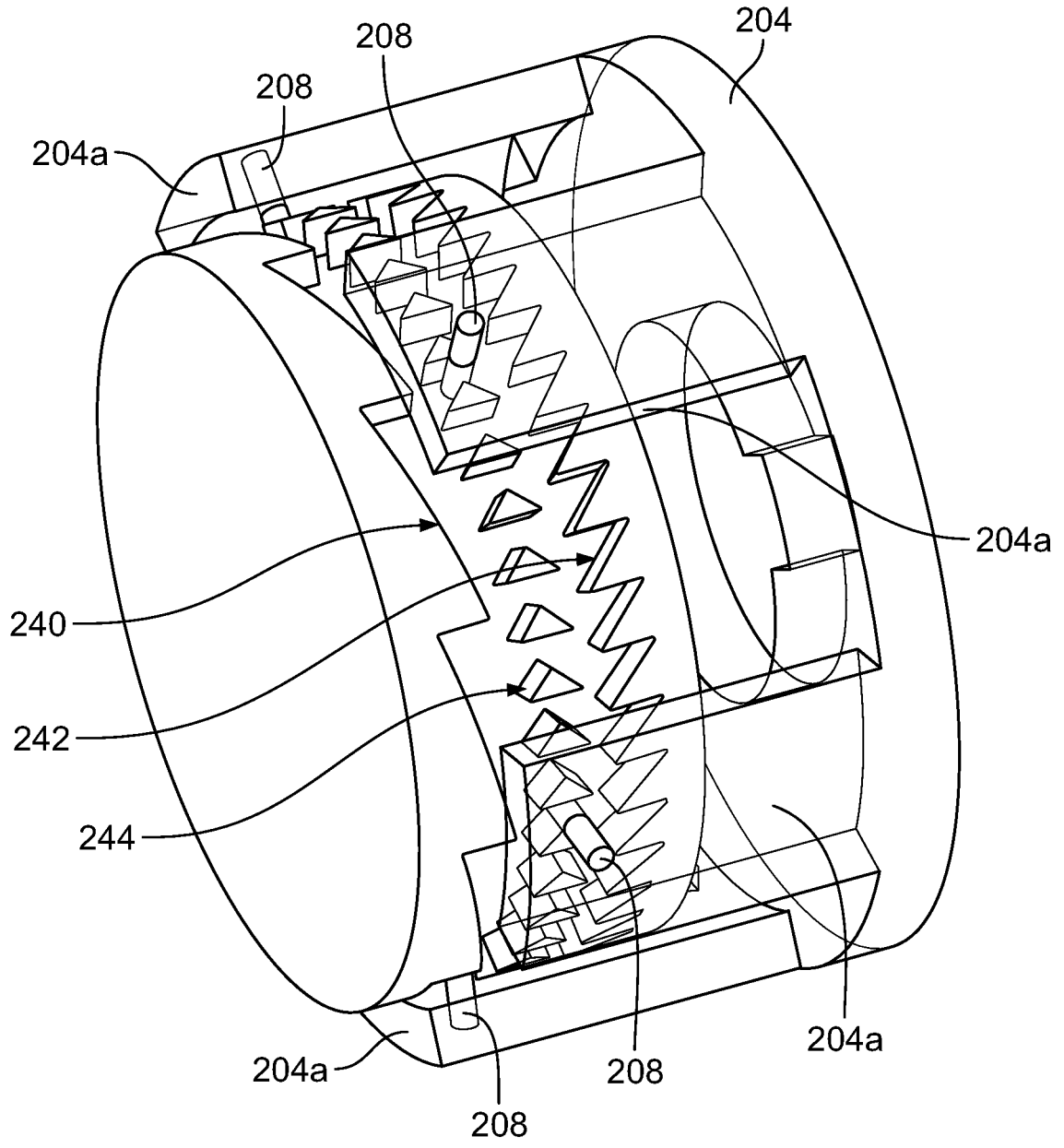
FIG. 10 shows us perspective view of a second embodiment of the invention wherein the slider element is configured with two tracks capable of rotationally moving the header two different angular distances during each cycle.

FIG. 10 shows a second embodiment of the invention wherein cylindrically-shaped slider element 206 defines two zig-zag-shaped tracks, a larger track 240 and a smaller track 242, within channel 216 on the circumferential surface thereof. This embodiment may be referred to as a dual dose actuator. Movement of pegs 208 through each respective track provides a different angular displacement of header element 204 and therefore a different rotation of output shaft 228 for each cycle of the drive mechanism. This allows the delivery of either a larger or a smaller volume of the liquid drug during each cycle of drive mechanism 200, depending on which way slider element 206 is pulled/pushed. As such, the total desired amount of the liquid drug can be delivered using as many cycles forcing pins 208 through larger track 240 as possible, with the remainder of the desired volume of the liquid drug being delivered by forcing pegs 208 through smaller track 242. As such, the second embodiment having the two tracks 240, 242 defined within channel 216 can lower the overall number of cycles required to deliver the desired volume of the liquid drug, and, therefore, the overall energy consumption of the drug delivery device 100. In other words, the dual dose actuator enables the drive mechanism to deliver a certain volume of fluid using a smaller number of SMA wire pulses and reduce the electrical energy consumption without increasing the minimum deliverable fluid volume.

In this embodiment, slider element 206 has the ability to be pushed and/or pulled in either direction "A" or "B" along its longitudinal axis (see FIG. 11 and FIG. 12), to a first position or a second position, with the slider element 206 returning to the neutral position when the force required to move slider element 206 in either direction "A" or direction "B" has been removed. As can be seen in FIG. 10, the outer circumferential surface of slider element 206 defines a first zig-zag track 240 and a second zig-zag track 242 with offsets 244 disposed therebetween to guide the pegs 208. FIG. 10 shows the drive mechanism with the slider element 206 in the neutral position wherein the pegs 208 are disposed in the middle of the channel 216 near offsets 244.

Because channel 216 on the circumferential surface of slider element 206 defines two tracks 240, 242 along which the pegs 208 may travel through channel 216, the longitudinal movement of slider element 206 in either direction "A" or "B" results in different angular displacements of header element 204 and, as such, results in different volumes of the liquid drug being dispensed by the pump mechanism. Travel of the pegs 208 along larger track 240 results in a larger volume of the liquid drug being dispensed, while travel of the pegs 208 along smaller track 242 results in a smaller volume of the liquid drug being dispensed. As an example, the when the pegs 208 travel along larger track 240, the header element 204 may rotate 36° and, as a result, deliver 0.20 units of the liquid drug. However, when the pegs 208 travel along smaller track 242, header element 204 may only move 9° and, as a result, will dispense only 0.05 units of the liquid drug. As such, to deliver 1.1 units of the liquid drug requires 5 cycles wherein the pegs 208 travel along the larger track 240 and two cycles wherein the pegs 208 travel along the smaller track 242 (5*0.20+2*0.05). As would be realized, the larger and smaller tracks 240 and 242 respectively may be designed to provide different degrees of angular displacement of header element 204 than those described in the exemplary embodiments, and, thus, different volumes of the liquid drug being dispensed. The ability to deliver larger and smaller volumes of the liquid drug enables drug delivery device 100 to deliver a certain volume of the liquid drug using a smaller number of cycles (e.g., SMA wire pulses) and therefore reduces the electrical energy consumption without increasing the minimum deliverable volume of the liquid drug. In other words, the number of strokes or pulses may be reduced as compared with the single dose actuator described above, which may require 22 strokes or pulses to deliver 1.1 units of fluid (if delivering 0.05 units per pulse).

Figure 11:
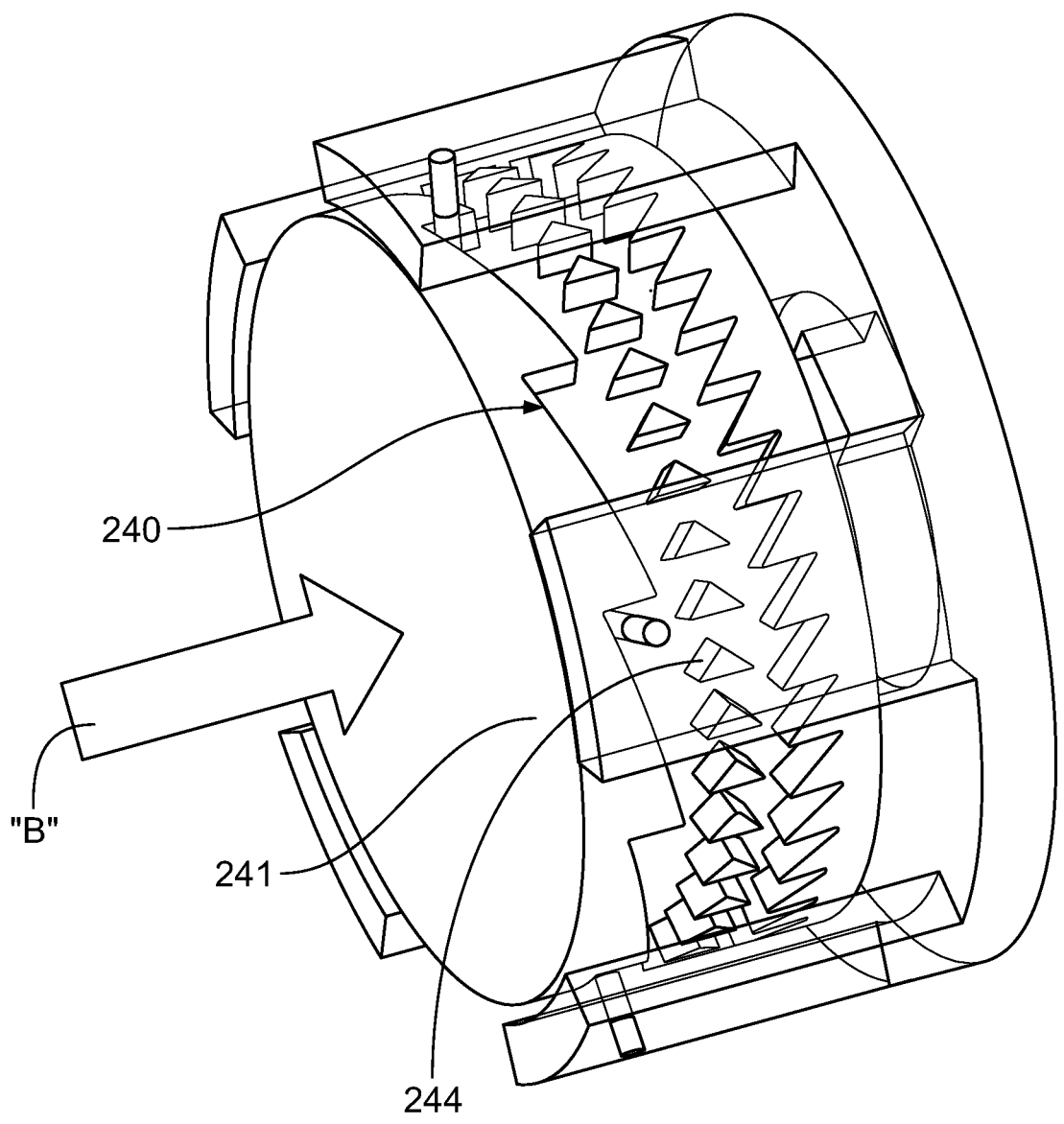
FIG. 11 is a perspective view of the second embodiment of the invention showing the interface elements being moved along a first, larger track in response to movement of the slider element back and forth between a neutral position and a first position, based on movement of the slider element in a first longitudinal direction.

FIG. 11 shows an example of drive mechanism 200 wherein pegs 208 travel along larger track 240. Movement of the slider element 206 in direction "B" from the neutral position to the first position, forces pegs 208 to move along the sloped portion 241 of larger track 240, thereby causing header element 204 to rotate through a larger angular distance. Movement of the slider element 206 back to the neutral position shown in FIG. 10 causes pegs 208 to engage the sloped surfaces of triangular-shaped offsets 244 nearest larger track 240 to move pegs 208 so as to position them to engage the next notch in the larger track 240 or the smaller track 242 during the next cycle, depending on whether slider element 206 is moved in direction "A" or direction "B".

Figure 12:
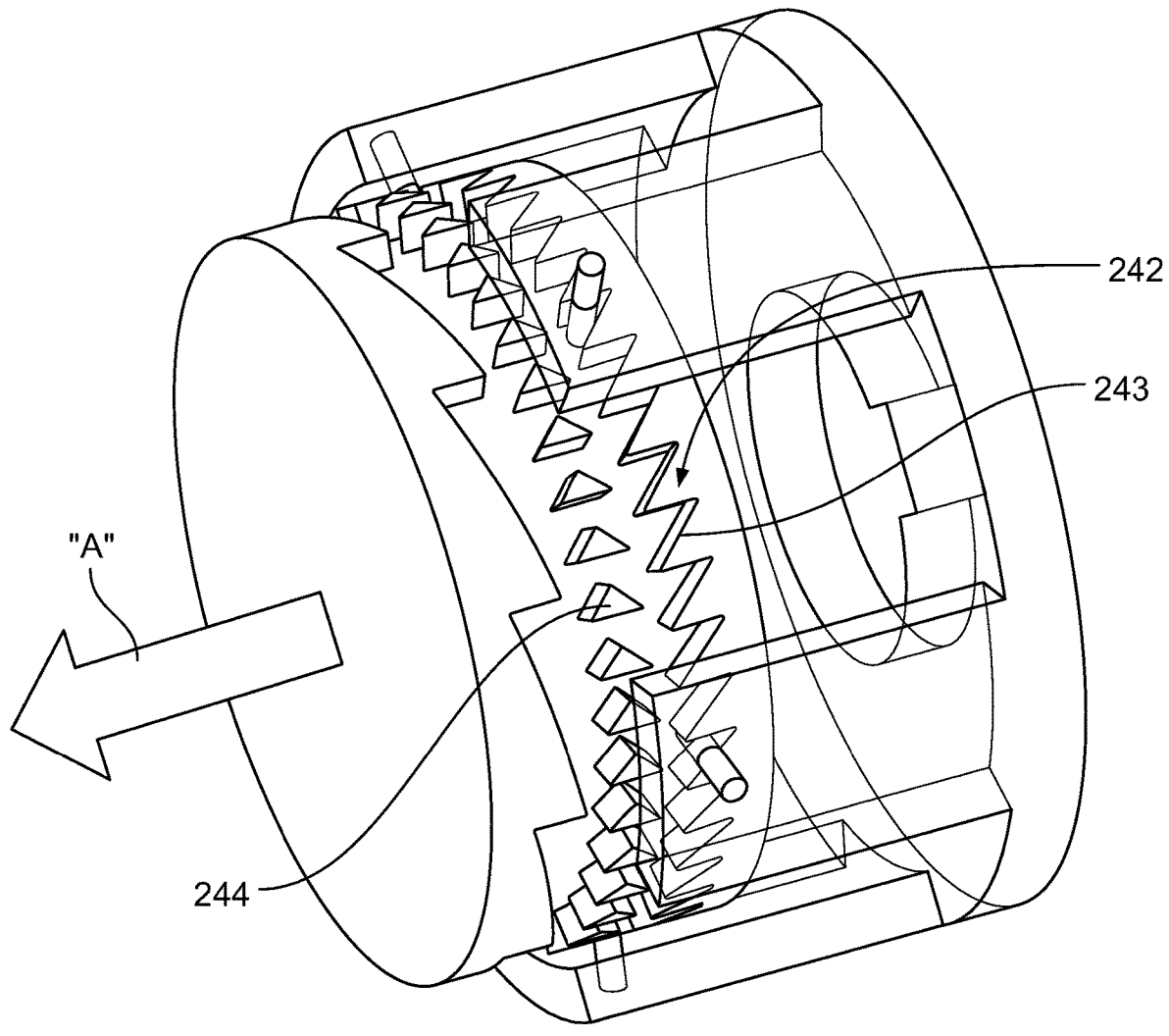
FIG. 12 is a perspective view of the second embodiment of the invention showing the interface elements being moved through a second, smaller track in response to movement of the slider element back and forth between a neutral position and a second position, based on movement of the slider element in a second longitudinal direction.

FIG. 12 shows an example of drive mechanism 200 wherein pegs 208 travel along smaller track 242. Movement of the slider element 206 in direction "A" forces pegs 208 to move along the sloped portion 243 of smaller track 242, thereby causing header element 204 to rotate through a smaller angular distance. Movement of the slider element 206 back to the neutral position shown in FIG. 10 causes pegs 208 to engage the sloped surfaces of triangular-shaped offsets 244 nearest smaller track 242 to move pegs 208 so as to position them to engage the next notch in the larger track 240 or the smaller track 242 during the next cycle, depending on whether slider element 206 is moved in direction "A" or direction "B".

Figure 13:
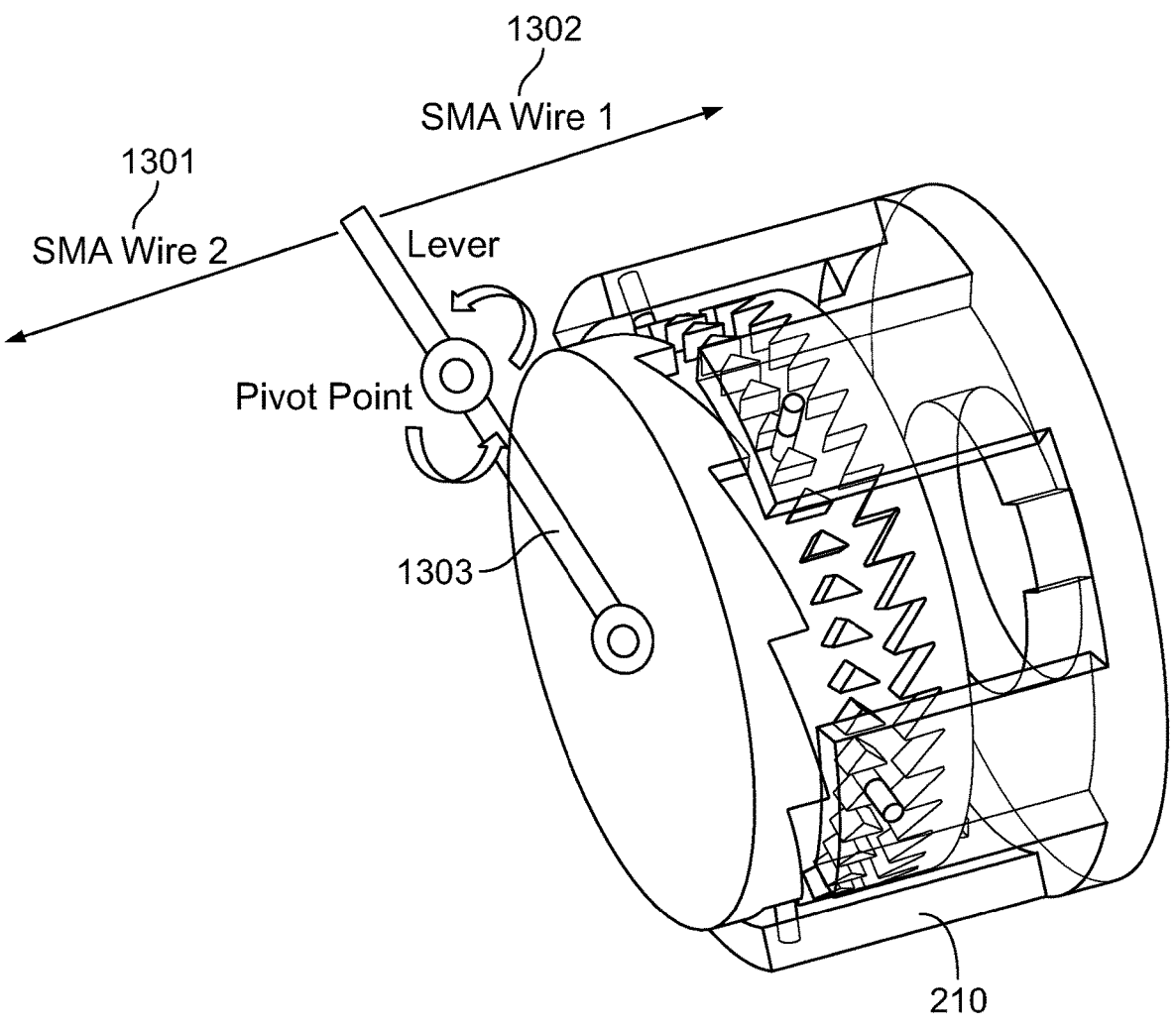
FIG. 13 is a perspective view of the second embodiment of the invention showing an arrangement for utilizing SMA wires and a linkage to provide motion of the slider element in the first and second longitudinal directions.

The ability to move slider element 206 in either direction "A" or "B" requires a means of applying a force in both directions. In one embodiment of the invention, two SMA wires 1301, 1302, shown in FIG. 13, may be used to provide the opposing forces. Each of SMA wires 1301, 1302 may be arranged such as to move a linkage 1303 in opposite directions, thereby providing a pulling or pushing force on slider element 206 to move it in either direction "A" or "B". The input mechanical advantage of the system can be adjusted by adjusting the distance between each SMA wire and the pivot point or between the pivot point and the center of the slider (i.e., a larger SMA force and a smaller SMA stroke or a smaller SMA force and a larger SMA stroke). Alternatively, depending on the type of gear train being used, SMA wires 1301, 1302 may be provided as direct connections to opposite surfaces of slider element 206 (not shown).

Figure 14:
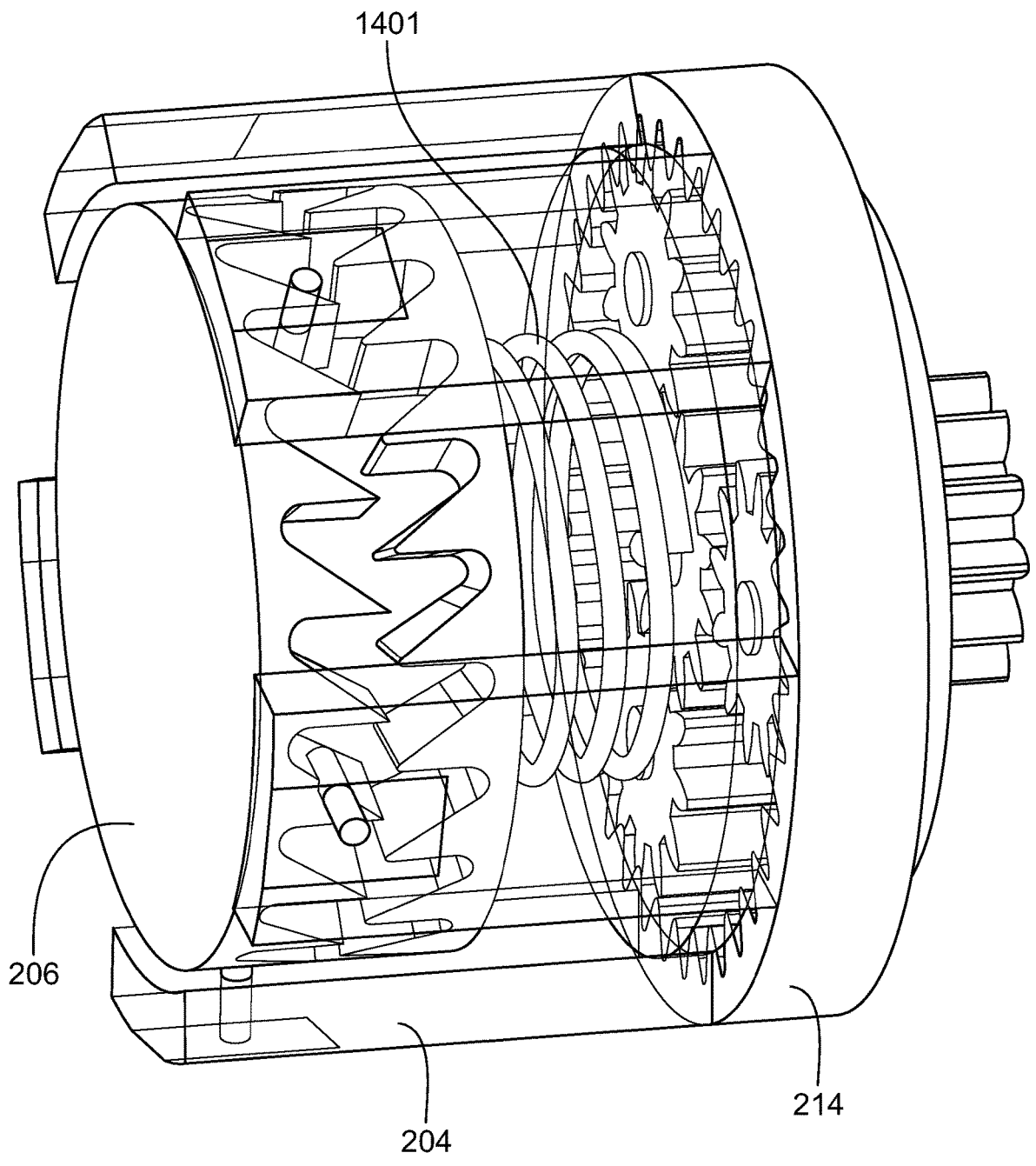
FIG. 14 is an alternate implementation of either the first or second embodiments showing the use of an internal spring to return the slider element to the neutral position.
Figure 15:
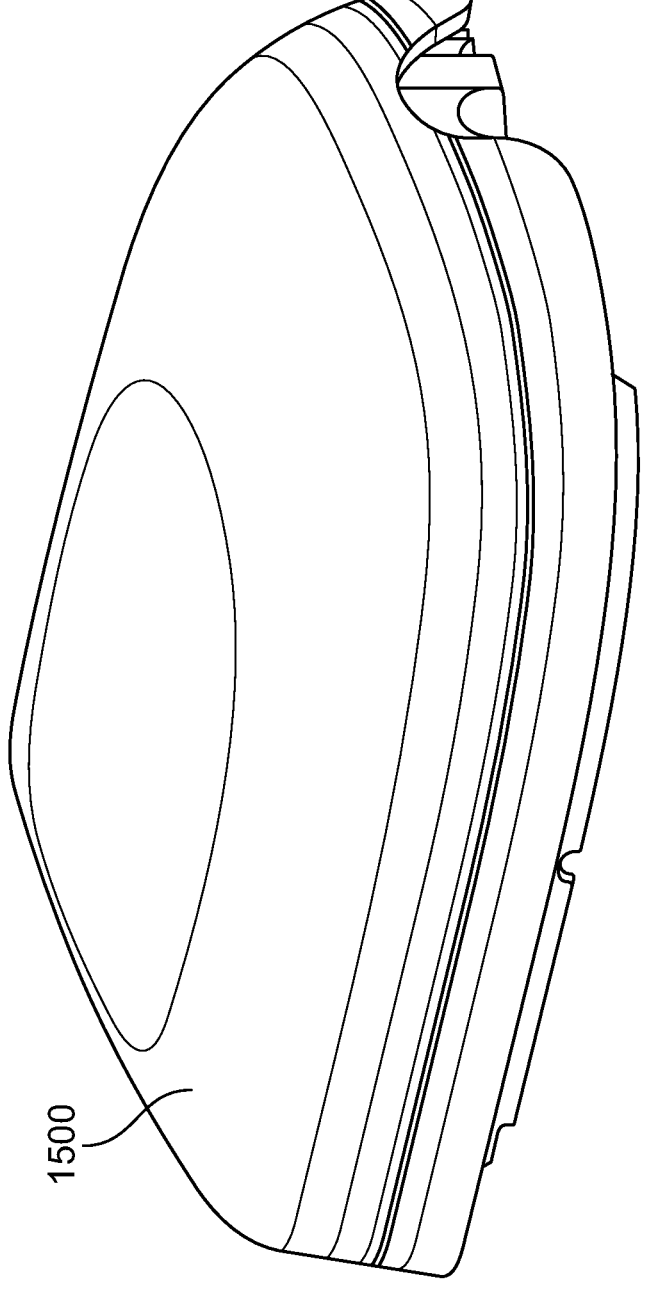
FIG. 15 is an example of a wearable drug delivery device with which the pumping mechanism disclosed herein may be used.

In one embodiment, slider element 206 may be returned to the neutral position via one or more springs, for example, spring 210 and/or an internal spring 1401 shown in FIG. 14. In other embodiments, SMA wires 1301, 1302 can be used to both move slider element 206 in directions "A" or "B" and to return slider element 206 to the neutral position. For example, SMA wire 1301 could be used to move slider element 206 in direction "A" and SMA wire 1302 could be used to move slider element 206 back to the neutral position. Likewise, SMA wire 1302 could be used to move slider element 206 in direction "B" and SMA wire 1301 could be used to move slider element 206 back to the neutral position.

FIG. 14 shows an alternative implementation of either the first or second embodiments of the invention in which the spring 1401 is internalized. Spring 1401 may provide either a tensive or compressive force against slider element 206 to return it to the neutral position. The use of the internal spring 1401 may replace the use of spring 210 shown in FIG. 2.

The following examples pertain to various embodiments of the pump mechanism suitable for use in a wearable drug delivery device:

Example 1 is a first embodiment of a drive mechanism comprising a slider element disposed coaxially with a header element, the slider element being cylindrical in shape and having a channel defined on the circumference thereof, the header having one or more tabs covering portions of the channel and one or more interface elements disposed between the slider element and the header element and extending into the channel.

Example 2 is an extension of Example 1, or any other example disclosed herein, wherein the interface elements are pegs extending from each tab.

Example 3 is an extension of Example 1, or any other example disclosed herein, wherein the interface elements are ball bearings disposed, wherein the channel has a semicircular cross section and wherein each tab defines hemispherical depression in which the ball bearing is disposed.

Example 4 is an extension of Example 1, or any other example disclosed herein, wherein the channel defines a zig-zag-shaped track such that longitudinal motion of the slider element causes the pegs to move through the channel, thereby causing rotation of the header element.

Example 5 is an extension of Example 4, or any other example disclosed herein, wherein the drive mechanism further comprises a spring, wherein the slider element is moved from a neutral position to a first position by application of a force and thereafter returns to the neutral position by action of the spring.

Example 6 is an extension of Example 5, or any other example disclosed herein, wherein the drive mechanism further comprises a wire composed of a shape memory alloy and coupled to the slider element, wherein the applied force generated by contraction of the wire.

Example 7, is an extension of Example 1, or any other example disclosed herein, where the zig-zag-shaped track comprises a series of opposing sloped walls such that movement of the slider element from a neutral position to a first position causes the pegs to follow one wall and movement of the slider element from the first position to the neutral position causes the peg to follow an opposing wall such that each peg moves in a zig-zag path within the channel as the slider element translates back and forth between the first position and the neutral position.

Example 8 is an extension of Example 7, or any other example disclosed herein, wherein the sloped portions of the opposing sloped walls have a linear profile.

Example 9 is an extension of Example 7, or any other example disclosed herein, wherein the sloped portions of the opposing sloped walls have a curved profile.

Example 10 is an extension of Example 1, or any other example disclosed herein, wherein the drive mechanism further comprises a gear train, coupled to the header element.

Example 11 is an extension of Example 10, or any other example disclosed herein, wherein the gear train is a planetary gear system and wherein the header element is coupled to a sun gear of the planetary gear system.

Example 12 is an extension of Example 11, or any other example disclosed herein, wherein an output shaft of the planetary gear system is coupled to a pump mechanism via a linkage, wherein the pump mechanism comprises a reservoir and a plunger which linearly translates within the reservoir by virtue of the rotation of the drive mechanism.

Example 13 is an extension of Example 5, or any other example disclosed herein, the drive mechanism further comprising a housing having the spring element being integrated therein.

Example 14 is an extension of Example 1, or any other example disclosed herein, wherein the channel defines first and second zig-zag-shaped tracks therein, wherein motion of the slider element in a first direction causes the pegs to follow the first track and movement of the slider element in a second, opposite direction causes the pegs to follow the second track, wherein the header element is displaced a different angular distances when the pegs follow the first track or the second track through the channel.

Example 15 is an extension of Example 14, or any other example disclosed herein, wherein the slider element is moved from the neutral position to either of the first or second positions by application of a force in a first or second direction respectively and thereafter wherein the slider element returns to the neutral position.

Example 16 is extension of Example 15, or any other example disclosed herein, wherein the first and second forces are provided by contraction of first and second wires composed of a shape memory alloy, respectively.

Example 17 is an extension of Example 16, or any other example disclosed herein, wherein the first and second wires are coupled to the slider element via a linkage.

Example 18 is an extension of Example 16, or any other example disclosed herein, wherein the slider element is moved from the first or second position to the neutral position by action of a first or second spring respectively.

Example 19 is an extension of Example 16, or any other example disclosed herein, wherein the slider element moves from the first or second position to the neutral position by action of one of the wires.

Example 20 is a pump mechanism comprising a reservoir, a plunger disposed in the reservoir and configured to translate longitudinally therein, a drive mechanism and a linkage between the drive mechanism and the plunger, wherein the drive mechanism comprises a generally cylindrically-shaped slider element having a channel defined on the circumference, a header element disposed coaxially with the slider element and defining one or more tabs covering portions of the channel and one or more interface elements extending from one or more of the tabs and into the channel.

Example 21 is an extension of Example 20, or any other example disclosed herein, wherein the interface elements are pegs extending from each tab.

Example 22 is an extension of Example 20, or any other example disclosed herein, wherein the interface elements are ball bearings disposed, wherein the channel has a semi-circular cross section and wherein each tab defines a substantially hemispherical depression in which the ball bearing is disposed.

Example 23 is an extension of Example 20, or any other example disclosed herein, when the channel defines a zig-zag-shaped track such that longitudinal motion of the slider element with respect to the header element causes the pegs to move through the channel along the track causing an angular displacement of the header element with respect to the slider element.

Example 24 is an extension of Example 21, or any other example disclosed herein, wherein the channel defines first and second zig-zag-shaped tracks therein, wherein motion of the slider element in a first direction causes the pegs to follow the first track and movement of the slider element in the second direction causes the pegs to follow the second track, wherein the header element is displaced a different angular distance when the pegs follow the first track or the second track through the channel.

To those skilled in the art to which the invention relates, many modifications and adaptations of the invention may be realized. Implementations provided herein, including sizes, shapes, ratings and specifications of various components or arrangements of components, and descriptions of specific manufacturing processes, should be considered exemplary only and are not meant to limit the invention in any way. As one of skill in the art would realize, many variations on implementations discussed herein which fall within the scope of the invention are possible. Moreover, it is to be understood that the features of the various embodiments described herein were not mutually exclusive and can exist in various combinations and permutations, even if such combinations or permutations were not made express herein, without departing from the spirit and scope of the invention. Accordingly, the method and apparatus disclosed herein are not to be taken as limitations on the invention but as an illustration thereof. The scope of the invention is defined by the claims which follow.

The invention claimed is:

1. A drive mechanism comprising:
   a slider element, the slider element being generally cylindrical in shape and having a channel defined on a circumferential surface thereof;
   a header element disposed coaxial with the slider element; and
   one or more interface elements extending into the channel, wherein the channel defines a zig-zag-shaped track therein such that longitudinal motion of the slider element along a longitudinal axis thereof with respect to the header element causes the one or more interface elements to move through the channel, thereby causing an angular displacement of the header element with respect to the slider element.

2. The drive mechanism of claim 1, wherein the interface elements comprise one or more pegs, one peg extending from each of one or more tabs extending from a main body portion, the one or more tabs covering portions of the channel defined in the circumferential surface of the slider element, and into the channel.

3. The drive mechanism of claim 1, wherein the channel is semicircular in cross-sectional shape, the interface elements comprising one or more ball bearings, each ball bearing disposed partially in the channel and partially in a substantially hemispherical depression defined in each of one or more tabs extending from a main body portion, the one or more tabs covering portions of the channel defined in the circumferential surface of the slider element.

4. The drive mechanism of claim 1, further comprising:
a spring;
wherein the slider element is moved in a first longitudinal direction with respect to the header element from a neutral position to a first position by an applied force in the first longitudinal direction and further wherein the slider element thereafter returns to the neutral position by action of the spring.

5. The drive element of claim 4, further comprising:
a wire composed of a shape memory alloy coupled to the slider element;
wherein the applied force is generated by contraction of the wire.

6. The drive mechanism of claim 1, wherein the zig-zag-shaped track comprises a series of opposing sloped walls such that a longitudinal movement of the slider element from the neutral position to the first position causes the one or more interface elements to follow one wall of the opposing series of sloped walls and longitudinal movement of the slider element from the first position to the neutral position causes the one or more interface elements to follow an opposing wall, such that each interface element moves in a zig-zag path within the channel as the slider element translates back and forth between the first and neutral positions.

7. The drive mechanism of claim 6, wherein sloped portions of the opposing sloped walls have a linear or curved profile.

8. The drive mechanism of claim 1, further comprising a gear train, coupled to the header element, wherein the gear train is a planetary gear system, the header element being coupled to a sun gear of the planetary gear system.

9. The drive mechanism of claim 8, wherein an output shaft of the planetary gear system is coupled to a pump mechanism via a linkage, the pump mechanism comprising:
a reservoir, and
a plunger, coupled to the drive mechanism such that rotation of the output shaft of the drive mechanism causes the plunger to linearly translate within the reservoir.

10. The drive mechanism of claim 4, further comprising:
a housing, the slider element and header element disposed in the housing;
wherein the spring is integrated into the housing.

11. The drive mechanism of claim 1, wherein:
the channel defines a first zig-zag-shaped track therein such that motion of the slider element along a longitudinal axis thereof with respect to the header element in a first longitudinal direction from a neutral position to a first position causes the one or more interface elements to move through the channel a first distance, thereby causing a first angular displacement of the of the header element with respect to the slider element; and
the channel defines a second zig-zag-shaped track therein such that motion of the slider element along a longitudinal axis thereof with respect to the header element in a second longitudinal direction, opposite the first longitudinal direction, from the neutral position to a second position, causes the one or more interface elements to move through the channel a second distance, thereby causing an second angular displacement of the of the header element with respect to the slider element.

12. The drive mechanism of claim 11, wherein:
the slider element is moved from the neutral position to the first position by a first applied force and further wherein the slider element thereafter returns to the neutral position;
the slider element is moved from the neutral position to the second position by a second applied force and further wherein the slider element thereafter returns to the neutral position.

13. The drive mechanism of claim 12, further comprising:
a first wire composed of a shape memory alloy, for providing the first force; and
a second wire composed of a shape memory alloy, for providing the second force.

14. The drive mechanism of claim 13, wherein the first and second wires are coupled to the slider element via a linkage.

15. The drive mechanism of claim 13, wherein:
the slider element moves from the first position to the neutral position by action of a first spring; and
the slider element moves from the second position to the neutral position by action of a second spring.

16. The drive mechanism of claim 13, wherein:
the slider element moves from the first position to the neutral position by a force applied by the second wire; and
the slider element moves from the second position to the neutral position by a force applied by the first wire.

17. A pump mechanism comprising:
a reservoir comprising a tube-like structure having a first end and a second end, the second end configured with a fluid path;
a plunger, disposed in the reservoir, the plunger configured to translate longitudinally within the reservoir toward the second end;
a drive mechanism; and
a linkage between the drive mechanism and the plunger;
wherein the drive mechanism comprises:
a slider element, the slider element being generally cylindrical in shape and having a channel defined on a circumferential surface thereof;
a header element disposed coaxial with the slider element; and
one or more interface elements extending into the channel, wherein the channel defines a zig-zag-shaped track therein such that longitudinal motion of the header element along a longitudinal axis thereof with respect to the slider element causes the one or more interface elements to move through the channel, thereby causing an angular displacement of the slider element with respect to the header element.

18. A drug delivery pump comprising:
a reservoir configured to house a drug;
a needle or cannula configured to penetrate skin of a user;

a plunger, disposed in the reservoir and configured to translate longitudinally within the reservoir to cause a volume of the drug to be delivered through the needle or cannula;

a drive mechanism comprising a slider element; and a linkage between the drive mechanism and the plunger, wherein the drive mechanism is configured to deliver a first volume of drug when the slider element is moved in a first direction and a second volume of drug different from the first volume when the slider element is moved in a second direction opposite to the first direction.

\* \* \* \* \*